(12) United States Patent
Goldberger et al.

(10) Patent No.: US 7,608,042 B2
(45) Date of Patent: Oct. 27, 2009

(54) BLOOD MONITORING SYSTEM

(75) Inventors: Daniel Goldberger, Boulder, CO (US); Eric Shreve, Louisville, CO (US); Wayne Siebrecht, Golden, CO (US); Benny Pesach, Rosh Haayin (IL); Gidon Pesach, Kfar Vitkin (IL); Gabriel Bitton, Jerusalem (IL); Ron Nagar, Tel Aviv (IL)

(73) Assignee: IntelliDx, Inc., Santa Clara, CA (US)

( * ) Notice: Subject to any disclaimer, the term of this patent is extended or adjusted under 35 U.S.C. 154(b) by 513 days.

(21) Appl. No.: 11/048,108

(22) Filed: Feb. 1, 2005

(65) Prior Publication Data

US 2006/0079809 A1 Apr. 13, 2006

Related U.S. Application Data

(60) Provisional application No. 60/614,122, filed on Sep. 9, 2004.

(51) Int. Cl.
*A61B 5/00* (2006.01)
*A61B 5/02* (2006.01)
*G01B 35/00* (2006.01)
*G01B 35/08* (2006.01)
*G01B 27/26* (2006.01)
*G01B 1/00* (2006.01)

(52) U.S. Cl. ............... 600/366; 600/364; 600/365; 600/309; 600/481; 436/43; 436/52; 204/400; 204/403.01; 204/403.02; 204/409

(58) Field of Classification Search ............... 600/309, 600/345–366; 204/193, 194, 400, 403.01–403.15, 204/409, 196.02; 436/43–54

See application file for complete search history.

(56) References Cited

U.S. PATENT DOCUMENTS

| 2,483,924 | A | 10/1949 | Mouliner |
| 3,340,869 | A | 9/1967 | Bane |
| 3,469,577 | A | 9/1969 | Kater |
| 3,498,899 | A | 3/1970 | Kater et al. |

(Continued)

FOREIGN PATENT DOCUMENTS

JP 06317566 A2 11/1994

(Continued)

OTHER PUBLICATIONS

LifeScan Inc. 2001, "LifeScan makes getting accurate glucose results perfectly easy", printed from http://www.lifescan.net/pdf/hospitals/ss_technology.pdf.

(Continued)

*Primary Examiner*—Charles A. Marmor, II
*Assistant Examiner*—Navin Natnithithadha
(74) *Attorney, Agent, or Firm*—Morrison & Foerster LLP

(57) ABSTRACT

The present invention is directed towards apparatuses and methods for the automated measurement of blood analytes and blood parameters for bedside monitoring of patient blood chemistry. Particularly, the current invention discloses a programmable system that can automatically draw blood samples at a suitable programmable time frequency (or at predetermined timing), can automatically analyze the drawn blood samples and immediately measure and display blood parameters such as glucose levels, hematocrit levels, hemoglobin blood oxygen saturation, blood gases, lactate or any other blood parameter.

21 Claims, 25 Drawing Sheets

U.S. PATENT DOCUMENTS

| | | | |
|---|---|---|---|
| 3,539,300 A | 11/1970 | Stone | |
| 3,910,256 A | 10/1975 | Clark et al. | |
| 3,993,049 A | 11/1976 | Kater | |
| 4,077,395 A | 3/1978 | Woolner | |
| 4,094,822 A | 6/1978 | Kater | |
| 4,127,111 A | 11/1978 | Drolet | |
| 4,218,421 A | 8/1980 | Mack, Jr. et al. | |
| 4,240,438 A | 12/1980 | Updike et al. | |
| 4,258,717 A | 3/1981 | Bisera et al. | |
| 4,340,457 A | 7/1982 | Kater | |
| 4,411,792 A | 10/1983 | Babb | |
| 4,535,786 A | 8/1985 | Kater | |
| 4,573,968 A | 3/1986 | Parker | |
| 4,608,996 A | 9/1986 | Brown | |
| 4,657,027 A | 4/1987 | Paulsen | |
| 4,661,319 A * | 4/1987 | Lape | 422/100 |
| 4,696,309 A | 9/1987 | Stephan | |
| 4,743,228 A | 5/1988 | Butterfield | |
| 4,786,394 A * | 11/1988 | Enzer et al. | 204/401 |
| 4,796,644 A | 1/1989 | Polaschegg | |
| 4,838,855 A | 6/1989 | Lynn | |
| 4,871,439 A * | 10/1989 | Enzer et al. | 204/401 |
| 4,872,813 A | 10/1989 | Gorton et al. | |
| 4,878,896 A | 11/1989 | Garrison et al. | |
| 4,919,596 A | 4/1990 | Slate et al. | |
| 4,928,694 A | 5/1990 | Maxwell | |
| 4,934,369 A | 6/1990 | Maxwell | |
| 4,951,669 A | 8/1990 | Maxwell et al. | |
| 5,002,066 A | 3/1991 | Simpson et al. | |
| 5,019,974 A | 5/1991 | Beckers | |
| 5,035,704 A | 7/1991 | Lambert et al. | |
| 5,037,396 A | 8/1991 | Streeter | |
| 5,048,537 A | 9/1991 | Messinger | |
| 5,077,010 A | 12/1991 | Ishizaka et al. | |
| 5,096,669 A | 3/1992 | Lauks et al. | |
| 5,134,079 A * | 7/1992 | Cusack et al. | 436/53 |
| 5,135,489 A | 8/1992 | Jepson et al. | |
| 5,148,811 A | 9/1992 | Messinger | |
| 5,165,406 A | 11/1992 | Wong | |
| 5,178,603 A | 1/1993 | Prince | |
| 5,195,963 A | 3/1993 | Yafuso et al. | |
| 5,216,597 A | 6/1993 | Beckers | |
| 5,225,063 A | 7/1993 | Gumbrecht et al. | |
| 5,237,993 A * | 8/1993 | Skrabal | 600/309 |
| 5,252,213 A | 10/1993 | Ahmad et al. | |
| 5,271,815 A | 12/1993 | Wong | |
| 5,307,263 A | 4/1994 | Brown | |
| 5,325,853 A | 7/1994 | Morris et al. | |
| 5,325,867 A * | 7/1994 | Skrabal et al. | 600/309 |
| 5,330,634 A | 7/1994 | Wong et al. | |
| 5,335,658 A | 8/1994 | Bedingham | |
| 5,345,932 A | 9/1994 | Yafuso et al. | |
| 5,368,029 A | 11/1994 | Holcombe et al. | |
| 5,368,555 A | 11/1994 | Sussman et al. | |
| 5,379,764 A | 1/1995 | Barnes et al. | |
| 5,380,665 A * | 1/1995 | Cusack et al. | 436/53 |
| 5,421,328 A | 6/1995 | Bedingham | |
| 5,431,174 A | 7/1995 | Knute | |
| 5,462,052 A | 10/1995 | Gehrich et al. | |
| 5,505,828 A | 4/1996 | Wong et al. | |
| 5,531,672 A | 7/1996 | Lynn | |
| 5,536,249 A | 7/1996 | Castellano et al. | |
| 5,569,186 A | 10/1996 | Lord et al. | |
| 5,582,184 A | 12/1996 | Erickson et al. | |
| 5,638,828 A | 6/1997 | Luaks et al. | |
| 5,665,065 A | 9/1997 | Colman et al. | |
| 5,695,623 A | 12/1997 | Michel et al. | |
| 5,697,366 A | 12/1997 | Kimball et al. | |
| 5,697,899 A | 12/1997 | Hillman et al. | |
| 5,720,924 A | 2/1998 | Eikmeier et al. | |
| 5,741,211 A | 4/1998 | Renirie et al. | |
| 5,741,554 A * | 4/1998 | Tisone | 427/424 |
| 5,743,960 A * | 4/1998 | Tisone | 118/683 |
| 5,746,217 A | 5/1998 | Erickson et al. | |
| 5,747,666 A | 5/1998 | Willis | |
| 5,758,643 A * | 6/1998 | Wong et al. | 210/542 |
| 5,800,387 A | 9/1998 | Duffy et al. | |
| 5,804,048 A | 9/1998 | Wong et al. | |
| 5,820,570 A | 10/1998 | Erickson et al. | |
| 5,871,494 A | 2/1999 | Simons et al. | |
| 5,902,253 A * | 5/1999 | Pfeiffer et al. | 600/309 |
| 5,916,524 A * | 6/1999 | Tisone | 422/100 |
| 5,928,880 A | 7/1999 | Wilding et al. | |
| 5,932,175 A | 8/1999 | Knute et al. | |
| 5,947,911 A | 9/1999 | Wong et al. | |
| 5,971,941 A | 10/1999 | Simons et al. | |
| 5,976,085 A | 11/1999 | Kimball et al. | |
| 6,017,318 A * | 1/2000 | Gauthier et al. | 600/578 |
| 6,027,479 A | 2/2000 | Alei et al. | |
| 6,036,924 A | 3/2000 | Simons et al. | |
| 6,066,243 A | 5/2000 | Anderson et al. | |
| 6,071,294 A | 6/2000 | Simons et al. | |
| 6,080,116 A | 6/2000 | Erickson et al. | |
| 6,099,484 A | 8/2000 | Douglas et al. | |
| 6,113,554 A | 9/2000 | Gilcher et al. | |
| 6,117,290 A | 9/2000 | Say et al. | |
| 6,123,827 A | 9/2000 | Wong et al. | |
| 6,128,519 A | 10/2000 | Say | |
| 6,175,752 B1 | 1/2001 | Say et al. | |
| 6,184,029 B1 | 2/2001 | Wilding et al. | |
| 6,188,648 B1 | 2/2001 | Olsen | |
| 6,192,891 B1 | 2/2001 | Gravel et al. | |
| 6,203,759 B1 | 3/2001 | Pelc et al. | |
| 6,233,471 B1 | 5/2001 | Berner et al. | |
| 6,251,660 B1 | 6/2001 | Muir et al. | |
| 6,272,364 B1 | 8/2001 | Kurnik | |
| 6,279,511 B1 | 8/2001 | Loughnane | |
| 6,296,615 B1 | 10/2001 | Brockway et al. | |
| 6,302,855 B1 | 10/2001 | Lay et al. | |
| 6,372,182 B1 | 4/2002 | Mauro et al. | |
| 6,375,627 B1 | 4/2002 | Mauze et al. | |
| 6,464,849 B1 | 10/2002 | Say et al. | |
| 6,472,220 B1 | 10/2002 | Simons et al. | |
| 6,484,046 B1 | 11/2002 | Say et al. | |
| 6,540,672 B1 | 4/2003 | Simonsen et al. | |
| 6,540,890 B1 | 4/2003 | Bhullar et al. | |
| 6,541,266 B2 | 4/2003 | Modzelewski et al. | |
| 6,546,269 B1 | 4/2003 | Kurnik | |
| 6,558,351 B1 | 5/2003 | Steil et al. | |
| 6,561,989 B2 | 5/2003 | Whitson | |
| 6,565,509 B1 | 5/2003 | Say et al. | |
| 6,572,545 B2 | 6/2003 | Knobbe et al. | |
| 6,576,101 B1 | 6/2003 | Heller et al. | |
| 6,595,919 B2 | 7/2003 | Berner et al. | |
| 6,602,205 B1 | 8/2003 | Erickson et al. | |
| 6,602,702 B1 | 8/2003 | McDevitt et al. | |
| 6,605,471 B1 | 8/2003 | Lundsgaard et al. | |
| 6,612,111 B1 | 9/2003 | Hodges et al. | |
| 6,645,359 B1 | 11/2003 | Bhullar et al. | |
| 6,653,091 B1 | 11/2003 | Dunn et al. | |
| 6,656,114 B1 | 12/2003 | Poulsen et al. | |
| 6,656,428 B1 | 12/2003 | Clark et al. | |
| 6,659,959 B2 | 12/2003 | Brockway et al. | |
| 6,666,821 B2 | 12/2003 | Kelmel | |
| 6,669,663 B1 | 12/2003 | Thompson | |
| 6,695,803 B1 | 2/2004 | Robinson et al. | |
| 6,723,288 B2 * | 4/2004 | Devlin et al. | 422/65 |
| 6,736,783 B2 | 5/2004 | Blake et al. | |
| 6,740,072 B2 | 5/2004 | Starkweather et al. | |
| 6,743,633 B1 | 6/2004 | Hunter | |
| 6,749,567 B2 | 6/2004 | Davis et al. | |
| 6,755,807 B2 | 6/2004 | Risk, Jr. et al. | |
| 6,755,949 B1 | 6/2004 | Bhullar et al. | |
| 6,764,462 B2 | 7/2004 | Risk, Jr. et al. | |

| | | |
|---|---|---|
| 6,768,879 B2 | 7/2004 | Kosuge |
| 6,780,297 B2 | 8/2004 | Matsumoto et al. |
| 6,800,074 B2 | 10/2004 | Henley et al. |
| 6,814,843 B1 | 11/2004 | Bhullar et al. |
| 6,814,844 B2 | 11/2004 | Bhullar et al. |
| 6,824,533 B2 | 11/2004 | Risk, Jr. et al. |
| 6,849,237 B2 | 2/2005 | Housefield et al. |
| 6,866,758 B2 | 3/2005 | Bhullar et al. |
| 6,872,297 B2 * | 3/2005 | Mansouri et al. ............ 205/775 |
| 6,872,358 B2 | 3/2005 | Hagen et al. |
| 6,875,619 B2 | 4/2005 | Blackburn |
| 6,902,703 B2 | 6/2005 | Marquiss et al. |
| 6,911,182 B2 | 6/2005 | Tegeler et al. |
| 6,911,621 B2 | 6/2005 | Bhullar et al. |
| 6,923,764 B2 | 8/2005 | Aceti et al. |
| 6,988,996 B2 | 1/2006 | Roe et al. |
| 7,004,928 B2 | 2/2006 | Aceti et al. |
| 7,022,219 B2 * | 4/2006 | Mansouri et al. ............ 205/792 |
| 7,152,616 B2 | 12/2006 | Zucchelli et al. |
| 7,157,049 B2 | 1/2007 | Valencia et al. |
| 7,162,290 B1 | 1/2007 | Levin |
| 7,179,423 B2 | 2/2007 | Böhm et al. |
| 7,198,606 B2 | 4/2007 | Boecker et al. |
| 7,232,547 B2 | 6/2007 | Rusch et al. |
| 7,244,232 B2 * | 7/2007 | Connelly et al. ............ 600/309 |
| 7,244,393 B2 | 7/2007 | Kaylor et al. |
| 7,258,672 B2 | 8/2007 | Hansson et al. |
| 7,303,727 B1 | 12/2007 | Dubrow et al. |
| 7,338,802 B2 | 3/2008 | Frischauf et al. |
| 7,378,270 B2 | 5/2008 | Azarnia et al. |
| 2003/0191415 A1 | 10/2003 | Moerman et al. |
| 2004/0138688 A1 | 7/2004 | Giraud |
| 2005/0214881 A1 | 9/2005 | Azarnia et al. |
| 2006/0188407 A1 | 8/2006 | Gable et al. |
| 2006/0235348 A1 | 10/2006 | Callicoat et al. |
| 2006/0278537 A1 | 12/2006 | Cai et al. |
| 2006/0281187 A1 | 12/2006 | Emery et al. |

FOREIGN PATENT DOCUMENTS

| | | |
|---|---|---|
| WO | PCT/US91/02911 | 10/1991 |
| WO | WO 91/16416 A1 | 10/1991 |
| WO | PCT/IL02/00285 | 10/2002 |
| WO | WO 02/080762 A1 | 10/2002 |
| WO | PCT/US02/19060 | 12/2002 |
| WO | WO 02/100254 A2 | 12/2002 |
| WO | WO 02/100254 A3 | 12/2002 |
| WO | WO 03/080166 A1 | 10/2003 |
| WO | PCT/KR03/000398 | 6/2004 |
| WO | WO 2004/047642 A1 | 6/2004 |
| WO | WO 2004/052204 A1 | 6/2004 |
| WO | WO 2004/056269 A1 | 7/2004 |
| WO | WO-2007/137285 A2 | 11/2007 |
| WO | WO-2007/137285 A3 | 11/2007 |

OTHER PUBLICATIONS

"Safe and Accurate Blood Sampling in Surgery and Intensive Care", Edwards Lifesciences LLC (VAMP Plus). 2000, pp. 2-4, printed from http://www.edwards.com/NR/rdonlyres/8B42FA8A-225A-4204-BBE-3-6ED73A376CC2/0/1141VAMPPlus04Update.pdf.

"OneTouch SureStep Blood Glucose Monitoring System Owner's Manual", LifeScan, Inc. 2002, Rev. Apr. 2003, printed from http://www.lifescan.com/pdf/ss_ob.pdf.

"OneTouch SureStep Test Strips For use with OneTouch SureStep Meters", LifeScan Inc. 1996-2006, printed from http://www.lifescan.com/products/teststrips/surestep.

"OneTouch SureStep Lancing Devices For use with OneTouch SureStep Meters", LifeScan, Inc. 1996-2006, printed from http://www.lifescan.com/products.lancing/.

"Edward VAMP System Brochure", Edwards Lifesciences, Inc. 2002, printed from http://www.edwards.com/Products/PressureMonitoring/VAMPSystemBrochurePDF.htm.

International Search Report mailed on May 23, 2007, for PCT Application No. PCT/US2006/24167, filed on Jun. 20, 2006, one page.

International Search Report mailed on Aug. 27, 2007, for PCT Application No. PCT/US06/45359, filed on Nov. 27, 2006, one page.

International Search Report mailed on Sep. 24, 2007, for PCT Application No. PCT/US06/45440, filed on Nov. 27, 2006, one page.

Non-Final Office Action mailed on Aug. 18, 2008, for U.S. Appl. No. 11/288,031, filed on Nov. 28, 2005, seven pages.

International Preliminary Report on Patentability mailed on Dec. 16, 2008, for PCT Application No. PCT/US2006/045642, filed on Nov. 28, 2006, seven pages.

International Preliminary Report on Patentability mailed on Nov. 28, 2008, for PCT Application No. PCT/US/2007/069546, filed on May 23, 2007, five pages.

International Preliminary Report on Patentability mailed on Nov. 28, 2008, for PCT Application No. PCT/US2007/069542, filed on May 23, 2007, five pages.

International Search Report mailed on Jun. 10, 2008, for PCT Application No. PCT/US07/69542, filed on May 23, 2007, one page.

* cited by examiner

All Layers

Bottom Layer

Middle Layer

Top Layer

|  |  | Tube Diameter |  | [mm] |
|---|---|---|---|---|
|  |  | 2 | 1 | 0.5 |
| Bolus Length [cm] | 5 | 0.2 | 0.0 | 0.0 |
|  | 10 | 0.3 | 0.1 | 0.0 |
|  | 40 | 1.4 | 0.3 | 0.1 |
|  | 100 | 3.4 | 0.9 | 0.2 |
|  | 200 | 6.8 | 1.7 | 0.4 |

FIG. 12

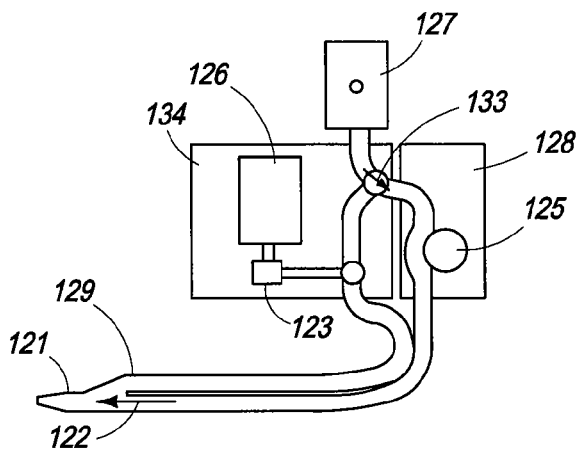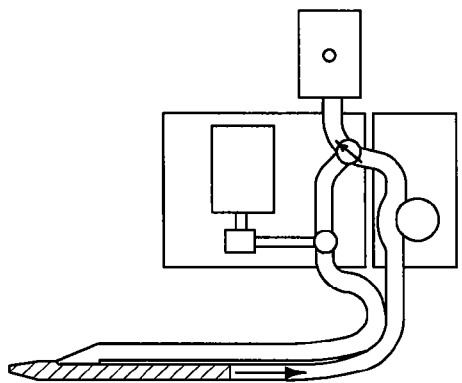
FIG. 13a        FIG. 13b
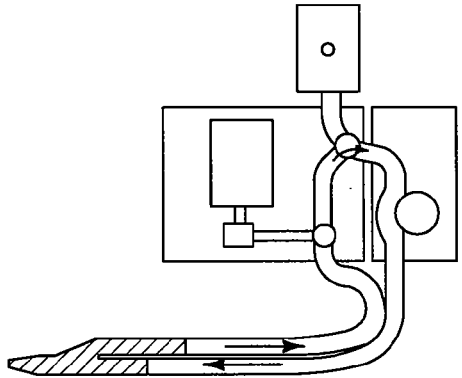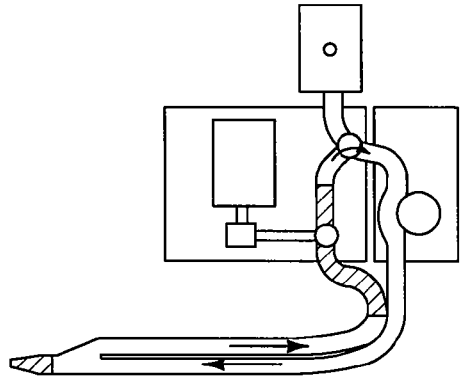
FIG. 13c        FIG. 13d
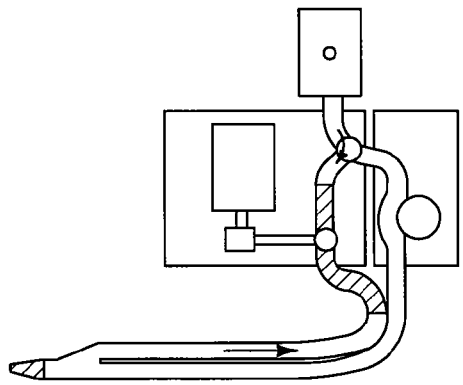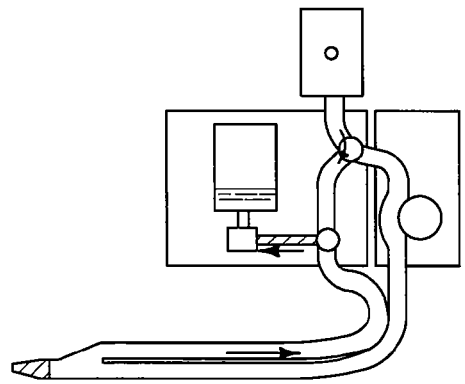
FIG. 13e        FIG. 13f

BLOOD MONITORING SYSTEM

CROSS-REFERENCE TO RELATED APPLICATIONS

The present invention relies on, for priority, U.S. Provisional Application No. 60/614,122, entitled "Blood Monitoring System", filed on Sep. 29, 2004.

FIELD OF THE INVENTION

The present invention relates generally to systems and methods for monitoring blood constituents, and in particular, to improved methods and systems for integrating a blood monitoring system with a patient fluid delivery infusion system for periodically measuring blood analytes and parameters using electrochemical, photochemical, optical techniques or a combination of the above techniques.

BACKGROUND OF THE INVENTION

Conventional methods and techniques for delivering drugs to a patient when the drugs cannot be orally administered include a) injection via a syringe and b) continuous delivery of medication, typically intravenously. Syringe injections have serious drawbacks, including risks of overdose and frequent injections to the patient, depending on patient need. Intravenous (IV) delivery systems require complicated and tedious interconnections. The medications are often delivered in a large dose through injection into the IV lines.

The infusion fluid delivery system has since added an alternative to these traditional drug delivery techniques. The infusion fluid delivery pump can be used to administer drugs to a patient in small, predetermined doses. The infusion pump can be controlled electronically to administer measured quantities of a drug at predetermined time periods to deliver an infusion of the medication to a patient. For example, U.S. Pat. No. 4,919,596, assigned to IVAC Holdings, describes a fluid delivery monitoring and control apparatus for use in a medication infusion system.

Specifically, the '596 patent discloses "a fluid delivery monitoring and control apparatus for use in a medical infusion system employing a disposable fluid pathway and cassette, which cassette contains a plurality of fluid channels, each of which includes a positive displacement pump having a piston mounted for reciprocating movement within a chamber and respective intake and outlet valves for controlling fluid flow through said chamber, the apparatus comprising: drive means for coupling to a cassette in association with a selected fluid channel including means for actuating said piston and said intake and outlet valves in a controlled sequence; encoding means coupled to the drive means for providing signals indicative of home position and rate of movement of said drive means; means for receiving rate command signals defining a desired rate of fluid flow through an associated cassette; means for ascertaining fluid flow rate from rate of movement signals and from cassette indicia indicating piston stroke volume and generating feedback signals indicative of sensed flow rate; and means for combining the rate command signals with said feedback signals to develop signals for controlling the drive means."

Since patient health requires the drawing of minimal amounts of blood, the prior art places the measurement units as close as possible to the infusion catheter. For example, in the case of an IV infusion fluid delivery and patient blood monitoring system, the measurement unit device must be located on or near the patient arm. As a result, prior art patient blood monitoring devices are cumbersome, especially when used during operation or in critical care units, where numerous other machines are present.

It has been recognized that in addition to infusion fluid delivery techniques, patient blood chemistry and monitoring of patient blood chemistry are important diagnostic tools in patient care. For example, the measurement of blood analytes and parameters often give much needed patient information in the proper amounts and time periods over which to administer a drug. Such measurements have previously been taken by drawing a patient blood sample and transporting such sample to a diagnostic laboratory. Blood analytes and parameters, however, tend to change frequently, especially in the case of a patient under continual treatment, as with infusion fluid delivery systems making this transport tedious.

For example, U.S. Pat. No. 4,573,968, also assigned to IVAC Holdings, discloses "a system for infusing fluid into a patient and for monitoring patient blood chemistry, comprising: an infusion line; a catheter at one end of said infusion line and adapted for insertion into the patient; a reversible infusion pump operable for pumping an infusion fluid through said infusion line and said catheter in a first direction for infusion into the patient; a blood chemistry sensor mounted in flow communication with said infusion line near said catheter for providing an indication of patient blood chemistry upon contact with a patient blood sample; and control means for controllably interrupting operation of said infusion pump in said first direction to interrupt supply of infusion fluid into the patient for a selected time interval; said control means further including means for operating said infusing pump for pumping infusion fluid through said infusion line in a second direction for drawing a patient blood sample through said catheter into contact with said sensor and then to resume operation in said first direction for reinforcing the drawn blood sample through said catheter into the patient followed by resumed infusion of said infusion fluid."

U.S. Pat. No. 5,758,643, assigned to Metracor Technologies, discloses "a method for monitoring a predetermined parameter of a patient's blood while infusing an infusion fluid through a sensor assembly and catheter into the patient, the method comprising: operating an infusion pump in a forward direction, to infuse the infusion fluid through the sensor assembly and catheter into the patient; interrupting infusion of the infusion fluid into the patient by operating the infusion pump in a reverse direction, to draw a blood sample from the patient through the catheter and into the sensor assembly; monitoring a signal produced by a first sensor of the sensor assembly and detecting a change in the signal indicative of the arrival of the blood sample at the first sensor; ceasing operation of the infusion pump in the reverse direction in response to detecting the arrival of the blood sample at the first sensor; and monitoring the first sensor signal while the blood sample is in sensing contact with the first sensor, to produce a measurement of a predetermined parameter of the patient's blood."

The prior art systems mentioned above, for both infusion fluid delivery systems and those infusion fluid delivery systems integrated with blood monitoring systems, include mechanisms for controlled fluid infusion and intermittent measurement of blood analytes, such as glucose levels. Such prior art systems typically use electrochemical sensors for sensing and measuring the levels of an analyte in a blood sample. For example, U.S. Pat. No. 6,666,821, assigned to Medtronic, Inc., discloses "a sensor system, comprising: a sensor to sense a biological indicator; a protective member located adjacent the sensor to shield the sensor from a surrounding environment for a selectable time period; and a processing circuit in communication with the sensor to receive a signal of the biological indicator and to indicate a therapy to be delivered."

The abovementioned prior art systems, however, have numerous disadvantages.

What is needed are improved methods and systems for arranging and using single use sensors. Additionally, what is needed are methods and systems that provide a plurality of tape and cassette configurations to improve the efficiency and effectiveness of blood monitoring.

In addition, what is needed are methods and systems for combining electrochemical sensor measurements with optical measurements to improve the accuracy and reliability of the system and for allowing anticoagulants to be administered to the patient without removing the apparatus.

What is also needed is a patient fluid infusion delivery system and blood monitoring device wherein the blood measurement unit is located near the infusion pump, for ease of use in a critical care or surgical environment.

What is also needed is a system in which the tube used for obtaining a blood sample is thin compared to the infusion tube, to minimize the amount of blood drawn.

Also needed is a programmable, automated system and method for obtaining blood samples for testing certain blood parameters and data management of measurement results, thus avoiding human recording errors and providing for central data analysis and monitoring. Ideally, such a system would be fully enclosed to protect patients and clinicians from sharp instruments and/or blood contaminated substrates.

SUMMARY OF THE INVENTION

The present invention is directed towards apparatuses and methods for automated measurement of blood analytes and blood parameters for bedside monitoring of patient blood chemistry. Particularly, the current invention discloses a programmable system that can automatically draw blood samples at a suitable programmable time frequency (or at predetermined timing), can automatically analyze the drawn blood samples and immediately measure and display blood parameters such as glucose levels, hematocrit levels, hemoglobin blood oxygen saturation, blood gasses, lactate or any other blood parameter.

The apparatus described in the current invention can be operated in connection to standard infusion sets and standard vascular access points, and is capable of automatically withdrawing blood samples for performing various blood tests. As described in detail in various embodiments, the automated blood monitoring system disclosed by the current invention can be operated in parallel with one or more infusion fluid delivery systems, with external pressure transducers or other devices connected to the same vascular access point without requiring any manual intervention during the blood sampling and measurement.

In one embodiment, the present invention includes a device for periodically monitoring at least one predetermined parameter of blood from a patient, comprising an access device for gaining access to said blood with a catheter, a pump to withdraw blood from the patient in a predetermined time schedule, a dispenser to dispense a small amount of blood and provide a blood sample, at least one sensor in contact with said blood sample, and a signal processor to measure a signal produced by the at least one sensor upon contact with the blood sample where the signal is indicative of said at least one predetermined parameter. The access device can be a catheter or an access device attached to a catheter.

Optionally, the dispenser and the at least one sensor are contained in a disposable cassette or cartridge. The at least one sensor is a single use sensor. The at least one single use sensor is a component of a manual test system. The at least one predetermined parameter is blood glucose and the at least one single use sensor is a glucose test strip. The at least one single use sensor is pre-calibrated. The at least one single use sensor produces measurements and the measurements are corrected by independent optical measurements of at least one blood parameter.

Optionally, the device automatically withdraws blood through the catheter and measures said signal from an undiluted blood sample and wherein said catheter is connected in parallel to at least one external line capable of being used for external infusion or capable of being used by an external pressure transducer. Optionally, the device is connected to a first lumen of a multiple lumen catheter having at least a first and second lumen and wherein flow in at least the second lumen is not stopped while withdrawing blood through said first lumen. Optionally, the signal processor produces measurements and wherein information derived from said measurements is automatically communicated to another device which can modify a therapy based on the measurement.

In another embodiment, the present invention includes a method for periodically monitoring at least one predetermined parameter of blood from a patient by accessing blood with a catheter, comprising the steps of automatically withdrawing blood from the patient in a predetermined time schedule, dispensing a small amount of blood through a dispenser, bringing at least one sensor in contact with the dispensed blood, and processing a signal produced by the sensor upon contact with the dispensed blood to measure said at least one parameter.

In one embodiment, the present invention is an automated system for periodically measuring blood analytes and blood parameters, the system comprising: an integrated monitor panel, a sensor cassette, and a control unit for controlling the periodic measurement of blood analytes and blood parameters, wherein said control unit further comprises a microprocessor unit; an internal communication link; an external communication link; and a signal analyzer, wherein the signal analyzer and at least one sensor in said sensor cassette enable the automatic measurement of blood analytes and blood parameters.

The present invention is also directed towards a method for periodically measuring blood analytes and blood parameters, the method comprising: programming a control unit for operating an automatic system for periodically measuring blood analytes and blood parameters, wherein said control unit further comprises a microprocessor unit; an internal communication link; an external communication link; and a signal analyzer, wherein the signal analyzer and an at least one sensor in a sensor cassette enable automatic measurement of blood analytes and blood parameters; and using an integrated monitor panel.

The present invention is also directed towards a method for periodically monitoring a predetermined parameter of blood, the method comprising: obtaining access to a vascular access point with a catheter; operating a pump to withdraw blood from a patient in a predetermined time schedule; dispensing a small volume of blood; advancing a first sensor to be in contact with the dispensed blood, wherein said first sensor is one of a plurality of sensors in a sensor cassette; and monitoring a signal produced by the first sensor upon contact with a patient blood sample to produce a measurement of one or a plurality of predetermined parameters of the patient blood sample.

The signal analyzer of the automated system for periodically measuring blood analytes and blood parameters converts measurement signals into a usable output, preferably indicative of blood chemistry. The control unit can also be programmed to periodically measure blood analytes and blood parameters via a predetermined time schedule for withdrawing a blood sample. The control unit can be programmed to withdraw blood at fifteen minute intervals. Optionally, the predetermined time schedule for withdrawing a blood sample is manually entered.

Preferably, the blood parameters measured in the system of the present invention include at least one of glucose, hematocrit, lactase, hemoglobin, oxygenation level or a combination thereof.

The automated system for periodically measuring blood analytes and blood parameters of the present invention also preferably comprises an automatic sampling interface mechanism for withdrawing a blood sample from a patient and bringing a blood volume to a sensor cassette. In a preferred embodiment, the sensor cassette is disposable and replaced periodically. The sensor cassette supports the use of at least one pre-calibrated single use sensor, and more preferably comprises a plurality of sensors arranged in a multiple layer tape structure.

Each single use sensor is advanced sequentially and positioned for direct contact with a blood sample through an advancement means, wherein the advancement means comprises a blood optical sensor for sensing the arrival and departure of undiluted blood within the sensor cassette.

The sensor employed in the automated system for periodically measuring blood analytes and blood parameters is an electrochemical sensor capable of detecting the presence of and enabling the measurement of the level of an analyte in a blood sample via electrochemical oxidation and reduction reactions at the sensor. Optionally, the sensor employed in the automated system for periodically measuring blood analytes and blood parameters is an optochemical sensor capable of detecting the presence of and enabling the measurement of the level of an analyte in a blood or plasma sample via optochemical oxidation and reduction reactions at the sensor.

Optionally, the sensor cassette may include a plurality of sensor cassettes, each comprising a different type of sensor.

In a preferred embodiment of the automated system for periodically measuring blood analytes and blood parameters of the present invention, the control unit controls, synchronizes, and checks the automatic operation of the system via the internal communication link.

The control unit of the automated system for periodically measuring blood analytes and blood parameters of the present invention is connected to a patient via a tubing structure connected to a catheter to transport fluids to and from a vascular access point, such as a vein or an artery. The tubing structure contains at least one or a plurality of lumens. In one embodiment, the tubing structure is multiple lumen, containing at least a first tube and a second tube, wherein the first tube is a standard infusion tube and the second tube is a blood sampling tube.

In another embodiment, the catheter of the automated system for periodically measuring blood analytes and blood parameters is connected to the vascular access point and a three-way junction. Thus, the system can control the operation of an external infusion delivery system attached to a vascular access point, which is shared with the automated system for periodically measuring blood analytes and blood parameters. Preferably, the automated system automatically blocks infusion during operation via the control unit. In addition, the control unit transmits command signals to deactivate external infusion fluid delivery system alarms when halting infusion during blood sampling and measurement. Subsequently, the control unit automatically resumes normal operation of infusion of the external infusion fluid delivery system.

Optionally, the control unit of the automated system for periodically measuring blood analytes and blood parameters provides feedback to the external infusion fluid delivery system in order to regulate an amount and a rate of infusing fluid into a patient.

Optionally, the automated system for periodically measuring blood analytes and blood parameters of the present invention further comprises a fluid container for storing and dispensing an anti-coagulant solution. The anti-coagulant solution is one of: heparin, Warfarin, or Coumadin.

Still optionally, the automated system for periodically measuring blood analytes and blood parameters further includes alerts and integrated test systems. The alerts may include alerts for detection of air in a line and detection of a blocked tube. In addition, the alerts may include alerts for hyperglycemia and hypoglycemia. The alerts may also include alerts for a hemoglobin level below a defined level.

Optionally, the control unit of the automated system for periodically measuring blood analytes and blood parameters enables input of user-defined ranges for blood parameters. Still optionally, the system alerts the user when the blood measurement falls outside of the user-defined ranges for blood parameters. Still optionally, the data from the system is correlated with other blood parameters to indicate an overall patient condition.

Optionally, the automated system for periodically measuring blood analytes and blood parameters may be wired or wireless. Still optionally, the control unit further comprises a battery compartment and at least one battery.

Optionally, the automated system for periodically measuring blood analytes and blood parameters further comprises a memory for storage of measurement results.

Still optionally, the automated system for periodically measuring blood analytes and blood parameters combines optical and electrochemical measurements. The combined measurement may include blood hematocrit levels and hemoglobin oxygenation levels. Further still, the combined measurement improves the accuracy of predicting whole blood glucose level from measured plasma glucose level.

In another embodiment, the present invention is an automated system for periodically measuring blood analytes and blood parameters, the system comprising: a signal analyzer, a sensor cassette, comprising at least one sensor; and an automatic blood sampling interface for withdrawing a blood sample and bringing the blood sample to the disposable sensor cassette, wherein the signal analyzer and at least one sensor enable automatic measurement of blood analytes and blood parameters.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following Detailed Description when considered in connection with the accompanying drawings, wherein:

FIG. 6b is an internal view of the fluid handling mechanism of the sensor cassette of the present invention as depicted in FIG. 6a;

FIG. 12 illustrates a table of blood bolus volumes in cubic centimeters according to the tube diameter in mm and its length in cm.

FIGS. 13a-13f depict another alternate embodiment of the automated blood analysis device of the present invention, optionally using a single channel infusion pump and an additional controlled valve;

DETAILED DESCRIPTION OF THE INVENTION

Figure 1A:
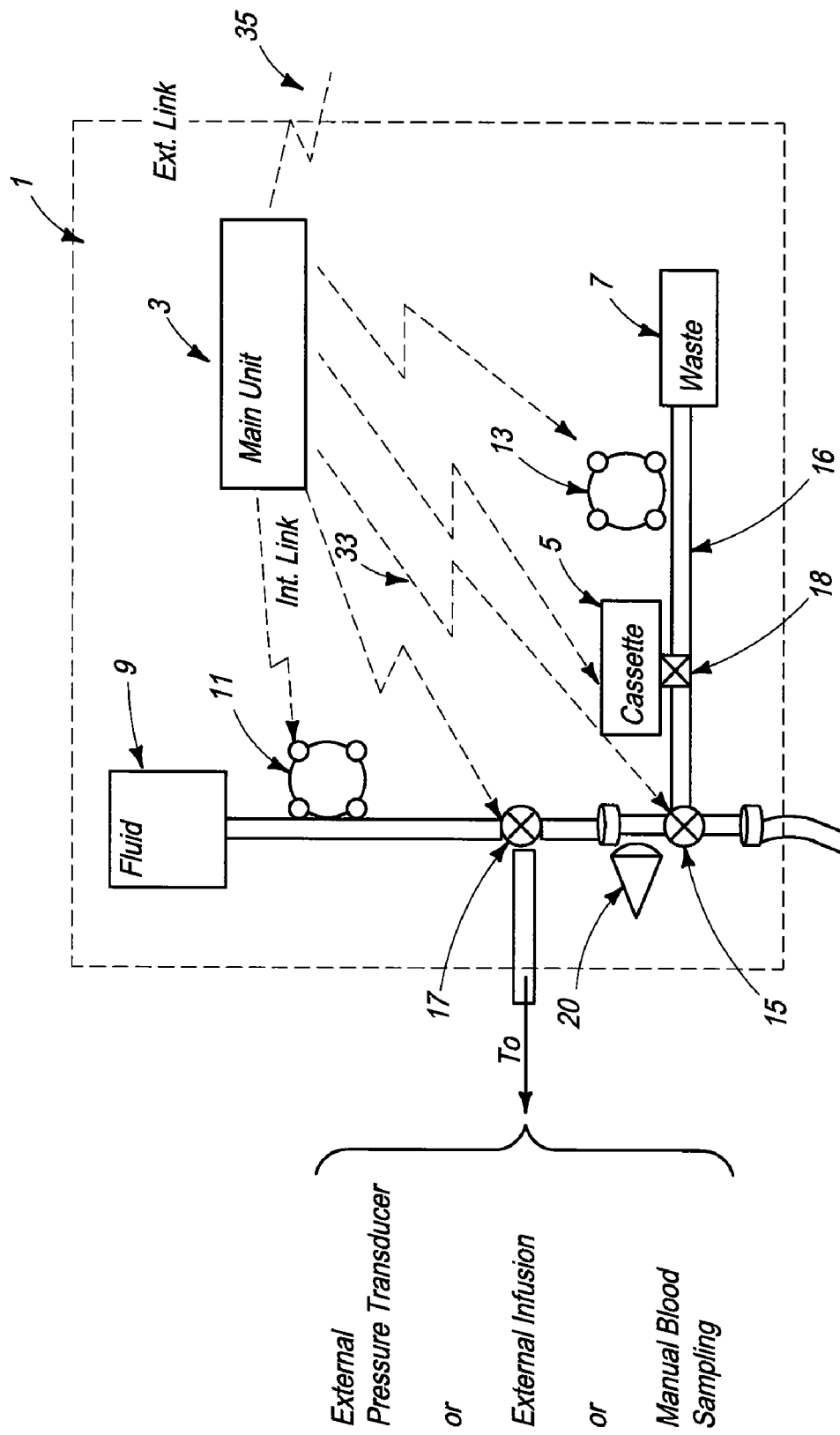
FIG. 1a illustrates one layout of the functional elements of a first exemplary embodiment of an automated device for analyzing blood parameters of the present invention.

The present invention is directed towards apparatuses and methods for automatically measuring blood analytes and blood parameters during bedside monitoring of patient blood chemistry. The system operates automatically to draw blood samples at suitable, programmable frequencies to analyze the drawn blood samples and obtain the desired blood optical and/or electrochemical readings such as glucose levels, hematocrit levels, hemoglobin blood oxygen saturation, blood gasses, lactates or any other parameter as would be evident to persons of ordinary skill in the art.

In particular, the apparatuses of the present invention may be operated in conjunction with standard infusion sets and are capable of automatically withdrawing blood samples for performing various blood measurements. As described in further detail below, various embodiments of the automated blood monitoring system can be automatically operated in parallel with infusion fluid delivery systems, external pressure transducers, or other devices connected to the same vascular access point without requiring manual intervention during blood sampling and measurement. Optionally, the automated blood analysis system and the infusion delivery system are integrated into a combined system. Still optionally, the automated blood analysis system of the present invention may include either a single lumen or multiple lumen tubing structure to transport fluids to and from the vascular access point.

In addition, the present invention is directed towards an automated system that includes a plurality of sensors (preferably single use sensors) that are packaged together in a cassette (also referred to as "sensor cassette" hereinafter). The sensors are preferably electrochemical or optochemical sensors, but other options such as sensors that support optical blood measurements (without relying on chemical reactions between the sample of blood and a chemical agent embedded in the sensor) are disclosed. The present invention also discloses apparatuses and methods that employ sensor components of manual test systems (e.g. blood glucose test strips) for use in an automated measurement system.

In performing a measurement, the system of the present invention automatically withdraws a blood sample through a vascular access point, such as an arterial or venous line, and advances a sensor in a sensor cassette to contact the drawn patient blood sample. When connected in parallel with an infusion fluid delivery line at the same vascular access point, the system automatically blocks the infusion fluid delivery until the blood sample is withdrawn, ensuring a "clean" and undiluted blood sample. A similar automated blocking mechanism is provided when the system is used with an arterial line and is used in parallel with an external pressure transducer. The automated blocking mechanism can be used in both automated blood analysis devices with single lumen tube structures and multiple lumen tube structures. The sensors produce a signal or a plurality of signals (based on electrochemical, optochemical, or optical response) that an analyzer, preferably a component of a manual test system, for example, but not limited to a blood glucose analyzer that uses blood glucose strips, transforms and/or converts to a readable output indicative of patient blood chemistry. Preferably, the readable output is displayed in less than or equal to thirty seconds. The system of the present invention can draw a blood sample as often as every minute, although it is preferably used at slower rates.

After completing the automatic blood measurement, the system may then optionally re-infuse at least part of the withdrawn blood into the patient and purge the tubing, if required. If connected in parallel to an infusion fluid delivery system, the system automatically resumes normal infusion operation until the next blood chemistry reading is desired. The apparatus may also dispose of at least a part of the withdrawn blood volume in a waste container. Optionally, the system disposes of the entire blood sample and simply resumes normal infusion operation.

The present invention is also directed towards a plurality of tape and cassette configurations that improve the efficiency and effectiveness of blood monitoring. The present invention also advantageously combines electrochemical sensor measurements with optical measurements of a plurality of blood parameters and analytes, including, but not limited to glucose, hematorcrit, heart rate, and hemoglobin oxygenation levels to improve the accuracy and reliability of the entire system.

The present invention is also directed towards a plurality of tubing and workflow configurations that can improve the efficiency and effectiveness of blood monitoring in various embodiments of the automated blood analysis system of the present invention. Either single lumen or multiple lumen tubing structures are attached to the catheter attached to the vascular access point. The tubing structure, as is described in further detail below, may vary depending upon functional and structural requirements of the system and are not limited to the embodiments described herein.

In addition, the present invention is directed towards features of the automated blood analysis device, such as, but not limited to storage of measurement results for trending or later download; alerts based on predefined levels or ranges for blood parameters; connectivity to external devices such as other monitors, external displays, external infusion pumps, etc; integration of the automated blood analysis device with an infusion pump that controls the rate and/or volume of fluids that are delivered to the patient; and integration of the automated blood analysis device with an infusion pump that controls the rate and/or volume of a substance that is delivered to the patient in order to regulate the rate of delivery according to the measured blood parameters in a closed-loop system.

As referred to herein, the terms "blood analyte(s)" and "blood parameter(s)" refers to such measurements as, but not limited to, glucose level; ketone level; hemoglobin level; hematocrit level; lactate level; electrolyte level (Na+, K+, CL−, Mg, Ca); blood gases ($pO_2$, $pCO_2$, pH); cholesterol; bilirubin level; and various other parameters that can be measured from blood or plasma samples. The term "vascular access point(s)" refer to venous or arterial access points in the peripheral or central vascular system.

Reference will now be made in detail to specific embodiments of the invention. While the invention will be described in conjunction with specific embodiments, it is not intended to limit the invention to one embodiment. Thus, the present invention is not intended to be limited to the embodiments described, but is to be accorded the broadest scope consistent with the disclosure set forth herein.

Referring now to FIG. 1a, a preferred layout of the functional elements of a preferred embodiment of an automated device for analyzing blood parameters of the present invention is illustrated. As shown in FIG. 1a, automated blood analysis device 1 is a device for automatically measuring blood analytes and blood parameters. Automated blood analysis device 1 is connected to a catheter or a venflon (not shown) leading to the patient 2, in order to automatically collect blood samples and automatically measure required blood parameters. Preferably, automated blood analysis device 1 comprises main unit 3; sensor cassette 5, which is preferably disposable; waste container 7; fluid container 9; first infusion pump 11; and second infusion pump 13.

Preferably, first infusion pump 11 and second infusion pump 13 are volumetric infusion pumps as are well-known in the art for use in intravenous fluid administration systems, although other types of pumps such as peristaltic pumps, piston pumps, or syringe pumps can also be used. Also, but not limited to such uses, it is preferred that first infusion pump 11 is used to control the flow in the fluid delivery line from fluid container 9 and second infusion pump 13 is used to control the flow in line 16 used for drawing blood samples to sensor cassette 5.

Automated blood analysis device 1 also comprises a series of tubes, including line 16, which are described in further detail below. In addition, automated blood analysis device 1 includes a first automated three-way stopcock 15 for controlling the flow inside line 16 and a second automated three-way stopcock 17 for controlling the flow of fluids to and from the external tubing and/or external devices. The operation of first stopcock 15 and second stopcock 17 is preferably fully automated and controlled by main unit 3. An automated sampling interface mechanism 18, described in further detail below, enables a blood sample to be brought automatically from line 16 to sensor 19 within sensor cassette 5.

As further described in detail, automated blood analysis device 1 can work as a stand-alone device, or can be connected in parallel with external infusions (on the same venous line) or external pressure transducers (on the same arterial line). A preferred location of connectivity is shown in FIG. 1a. Automated blood analysis device 1 enables blood sampling and analysis on demand.

With reference to FIG. 1a, the operational steps of automated blood analysis device 1 will now be described according to a preferred workflow when automated blood analysis device 1 is connected in parallel to external infusions at the same vascular access point. It is to be understood that such embodiment is exemplary but not limiting and that the automated blood analysis device 1 may be connected to other external devices at the same vascular access point. Automated blood analysis device 1 blocks the operation of any connected infusion and/or external device (such as an external pressure transducer) during the period of blood sampling, in order to ensure that the blood sample is not diluted/altered by other fluids injected in the patient.

During normal operation, first stopcock 15 blocks line 16 and keeps the line to patient 2 open and second stopcock 17 enables the external infusion to flow freely into patient 2 while at the same time blocking the line coming from fluid bag 9.

When performing automated blood sampling and measurement of required blood analytes, main unit 3 directs second stopcock 17 to block incoming external infusions and to open the line from fluid bag 9 to patient 2. Once the external infusions are interrupted, pump 11 draws blood from patient 2. The blood is drawn along the tube until the remaining infusion volume and the initially diluted blood volume passes first stopcock 15.

Main unit 3 calculates the required volume of blood to be withdrawn based on the diameter and length of the tubing and according to a programmable dead-space volume, which can be either pre-calibrated or user-defined. Optionally, a blood optical sensor 20 can be used to establish whether undiluted blood has reached the tube segment proximal to first stopcock 15. When undiluted blood reaches first stopcock 15, first stopcock 15 is repositioned to create an open line between patient 2 and sensor cassette 5. Blood is then pumped into line 16 via pump 13.

When undiluted blood reaches the tube segment proximal to sensor cassette 5, a blood sample is automatically taken inside sensor cassette 5 (by sampling interface mechanism 18) whereby a sensor 19 (from a plurality of sensors within sensor cassette 5) is placed into contact with the drawn blood sample. Sensor 19 is preferably, but not limited to, a single use sensor, and is used to measure patient blood analyte(s) and blood parameter(s). Sensor 19 is preferably a component of a manual test device, such as, but not limited to glucose test strips for measuring glucose levels.

While the blood sample is analyzed, blood withdrawal from patient 2 is stopped, main unit 3 reverses the operation of pump 11, and first stopcock 15 is repositioned to infuse blood back into patient 2. The tubing components, including line 16, are then flushed by purging fluid from fluid bag 9. Blood and fluids from line 16 are stored in waste container 7, which is, for example, but not limited to a waste bag generally used for storage of biological disposals. Optionally, the remaining blood in line 16 can be infused back into patient 2 by reversing the direction of pump 13. After purging both line 16 and the line between fluid bag 9 and patient 2, main unit 3 redirects first stopcock 15 and second stopcock 17 to block both line 16 and the line between fluid bag 9 and patient 2 and reopen the line from the external infusion device, into patient 2.

Referring back to FIG. 1a, in an alternate workflow of a preferred embodiment of the present invention, once enough blood is withdrawn and pumped to line 16, stopcock 15 is turned and the volume of blood in line 16 is pushed by the fluid coming from fluid bag 9. This method is referred to as using a "bolus of blood" and is designed to reduce the amount of blood withdrawn in line 16. The remaining steps in this alternate workflow are as described above with respect to the preferred embodiment in FIG. 1a and will not be repeated herein.

Figure 1B:
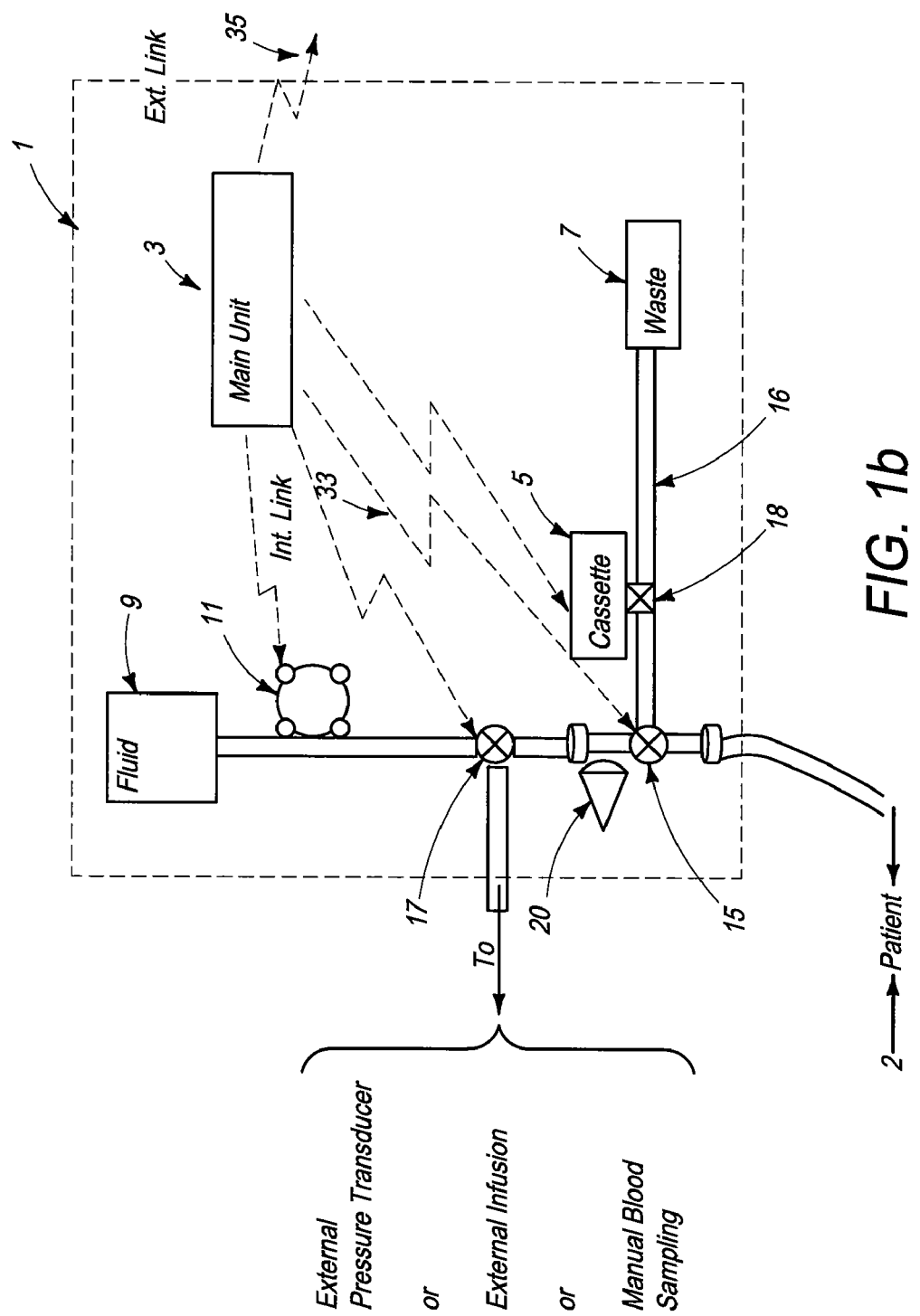
FIG. 1b illustrates the layout of the functional elements and workflow of a second embodiment of the blood analysis device of the present invention.

FIG. 1b illustrates the layout of the functional elements and workflow of a second preferred embodiment of the automated blood analysis device of the present invention. This embodiment will be described with reference to FIG. 1a, noting the differences between the designs. In the second preferred embodiment, automated blood analysis device 1 employs a single pump 11 and does not require the usage of second pump 13 (as shown in FIG. 1a). Operationally, an extra dead-space volume is initially withdrawn by single pump 11 to ensure that an undiluted blood volume has passed stopcock 15. When the undiluted blood volume passes stopcock 15, stopcock 15 is repositioned to create an open line between pump 11 and sensor cassette 5. The undiluted blood volume is then pushed into line 16 by pump 11. The remaining operational steps are not modified with respect to the embodiment illustrated in FIG. 1a, and thus will not be repeated herein.

Figure 1C:
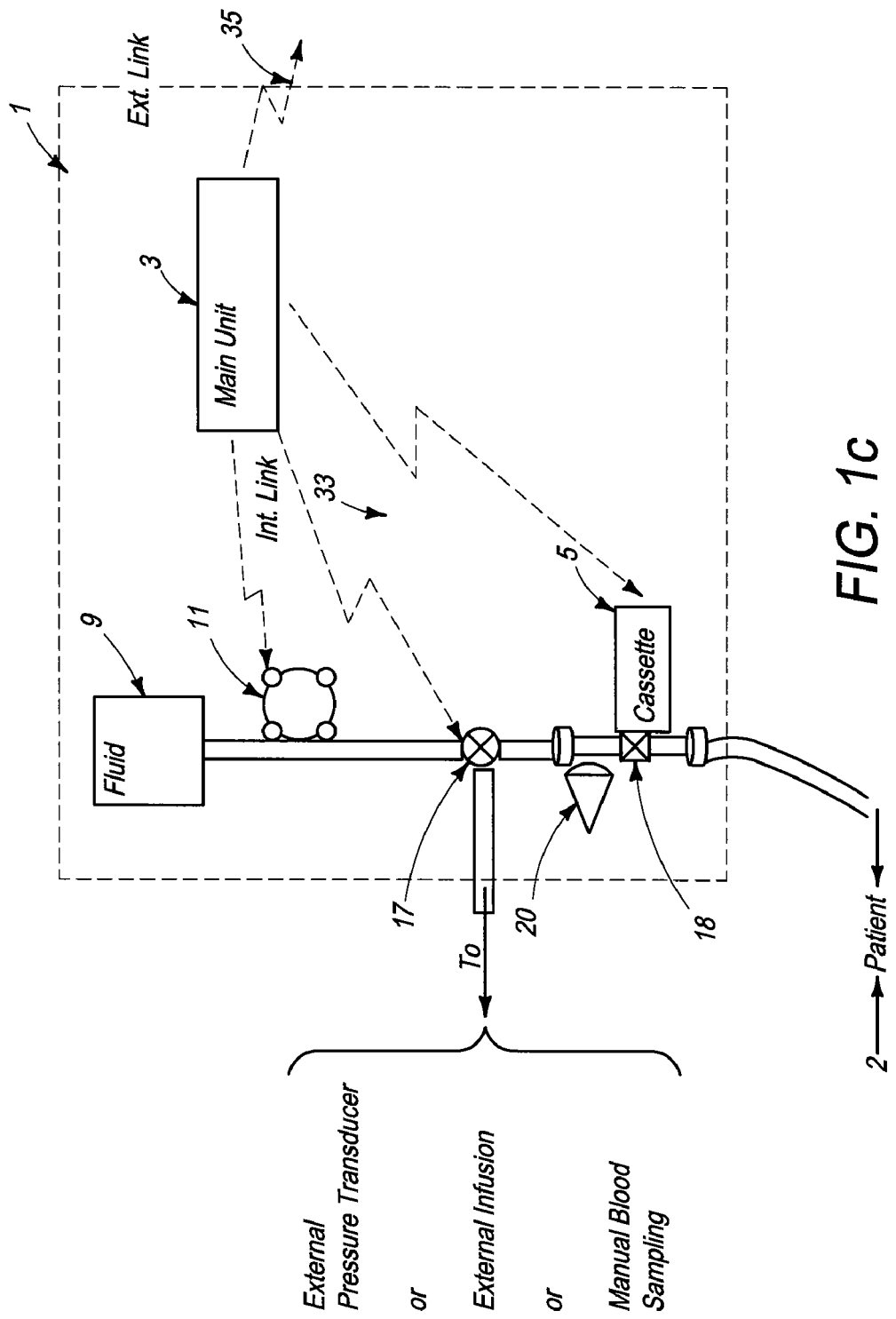
FIG. 1c illustrates the layout of the functional elements and workflow of a third embodiment of the blood analysis device of the present invention.

FIG. 1c illustrates the layout of the functional elements and workflow of a third preferred embodiment of the blood analysis device of the present invention. Again, this embodiment will be described with reference to FIG. 1a, noting the differences between the functionalities and structures. In the third preferred embodiment, sensor cassette 5 is directly attached to the main tube, thus eliminating the need for additional line 16. While many of the operational steps are not modified with respect to FIG. 1a, there are some operational differences in the third embodiment. For example, when the undiluted blood drawn by pump 11 reaches the tube segment proximal to sensor cassette 5, a blood sample is automatically drawn into sensor cassette 5 via sampling interface mechanism 18. In addition, the third preferred embodiment does not include stopcock 15, as shown in FIG. 1a.

Figure 1D:
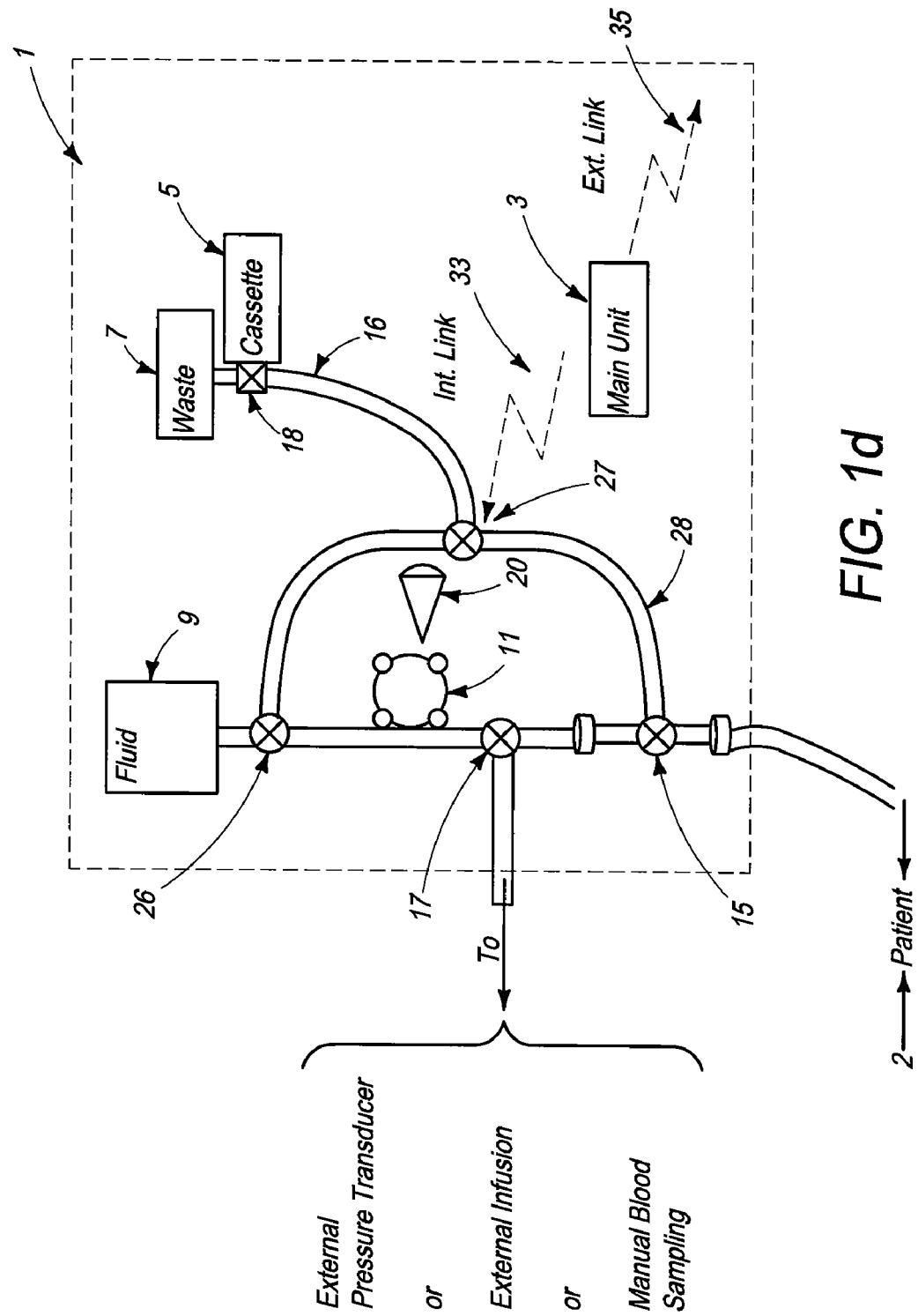
FIG. 1d illustrates the layout of the functional elements and workflow of a fourth embodiment of the blood analysis device of the present invention.

FIG. 1d illustrates the layout of the functional elements and workflow of a fourth preferred embodiment of the blood analysis device of the present invention. Again, this embodiment will be described with reference to FIG. 1a, noting the differences between the designs. In the fourth preferred embodiment of the blood analysis device of the present invention, the device comprises a single pump 11, two additional stopcocks 26 and 27, and line 28 positioned between stopcock 26 and stopcock 15. The operation of the fourth embodiment is described in further detail below. In order to withdraw blood into line 16, stopcock 15 is turned to block the main tube and blood is withdrawn above stopcock 27 by pump 11. Once the blood is drawn above stopcock 27, stopcock 27 is turned while the operation of pump 11 is reversed, thus pushing blood through stopcock 27 into line 16. The blood in the line is then flushed with purging fluid from fluid container 9. Stopcock 27 is then turned again, thus enabling infusion back into line 28.

Now referring back to FIGS. 1a, 1b, 1c, and 1d, the infusion tube and line 16, as used in the first and second embodiments 1a and 1b, respectively, can be made of commonly used flexible transparent plastic materials such as polyurethane, silicone or PVC. When line 16 is present in any particular embodiment, it is preferably of the smallest diameter possible, while still enabling blood flow without clotting or hemolysis. For example, and not limited to such example, line 16 has a diameter of less than or equal to 1 mm.

The tubing and stopcocks/valve sets of the present invention can be implemented in various designs to support operational requirements. Optionally, the tubing includes filter lines to enable elimination of air embolism and particle infusion. Additionally, the tubing can optionally include a three-way stopcock that enables the user/clinician to manually draw blood samples for laboratory tests. In addition, three-way stopcock 17 may optionally include a plurality of stopcocks at its inlet, each controlling a separate external line. In another optional embodiment, the positions of stopcock 15 and stopcock 17 can be interchanged, thus placing stopcock 17 closer to the vascular access point in patient 2 than stopcock 15 or cassette 5.

Preferably, automated blood analysis device 1 is connected to an insertion element, such as, but not limited to a catheter or a Venflon (not shown), inserted into a vein or artery to provide a flow path for fluid infusion and drawing of patient blood samples. Insertion into a vein or artery is performed according to existing clinical indications that are well known to those of ordinary skill in the art. This design avoids repeated insertions of needles or catheter structures into the patient as is commonly required with prior art blood chemistry monitoring techniques. Connection of the automated blood analysis device 1 to the catheter or venflon is made by standard means such as luer-lock connectors, as are known in the art. Optionally, the insertion element, catheter or venflon, can be part of the tubing of automated device for analyzing blood 1.

Figure 1E:
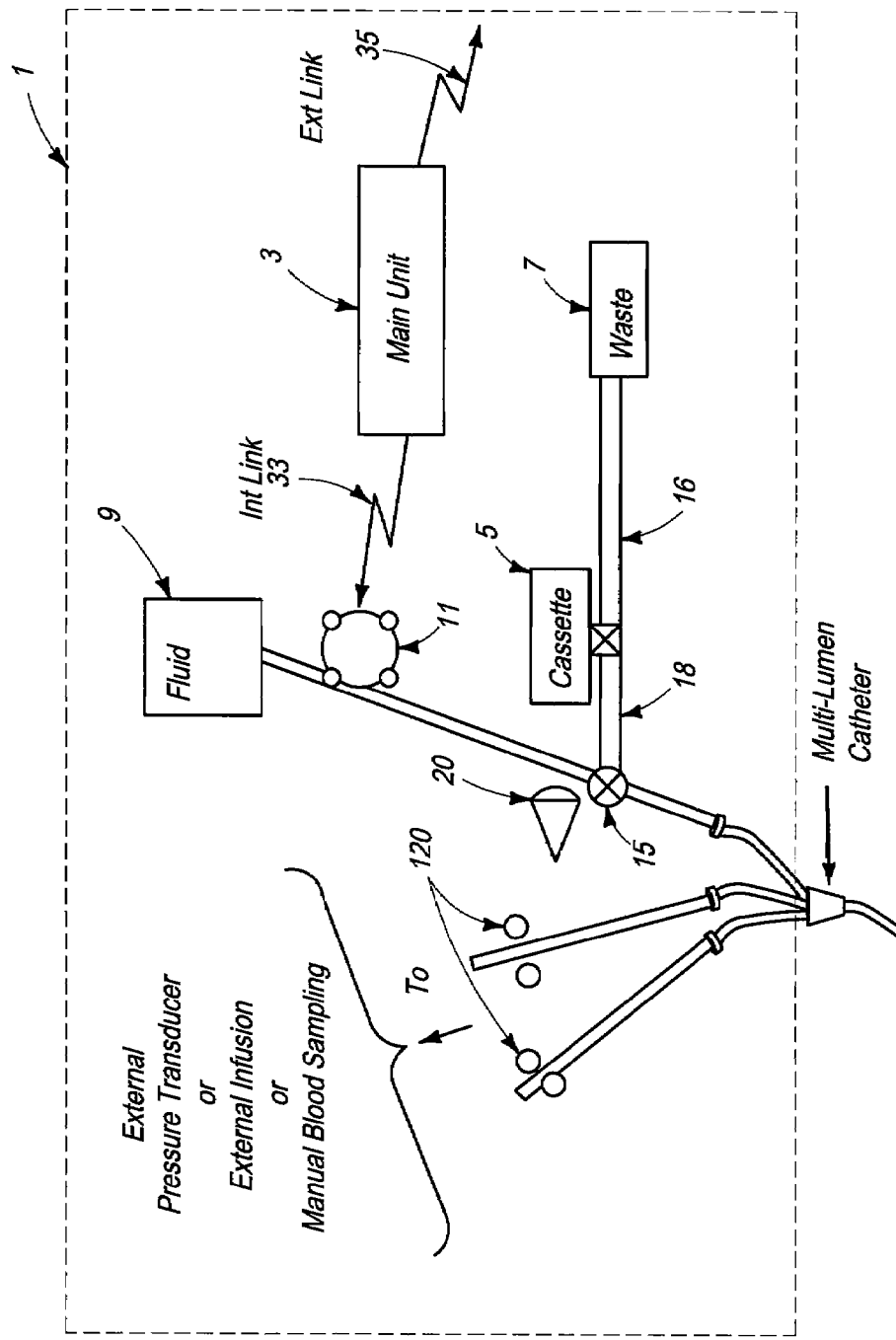
FIG. 1e illustrates the functional elements of an exemplary embodiment of the automated blood analysis device of the present invention, connected to a multi-lumen catheter.

In another optional embodiment, the catheter may comprise a multi-lumen catheter wherein one of the lumens is used for automatically drawing the blood sample. FIG. 1e illustrates the functional elements of an exemplary embodiment of an automated blood analysis device 1 that is connected to a multi-lumen catheter. As shown in FIG. 1e, the connection is formed between the automated blood analysis device and preferably the largest lumen of the multi-lumen catheter. The remaining lumens of the plurality of lumens are used for infusions or for measuring blood pressure by an external pressure transducer. The remaining lumens are automatically blocked during blood draw by external pinching components 120, one for each additional lumen. The other components of the system can be implemented as described above with reference to FIGS. 1a, 1b, 1c, and 1d. Optionally, when connecting automated blood analysis device 1 to the proximal lumen of the multi-lumen catheter, it is not necessary to stop other infusions while taking the blood sample, particularly when inserting the multi-lumen catheter in a vein with a high blood flow rate, such as, but not limited to, inserting a multi-lumen central vein catheter.

Fluid container 9 contains a fluid which preferably includes an anti-coagulant agent. The anti-coagulant solution is therefore added to the reinfused blood sample and is used for purging the tubes in order to prevent clotting of the patient blood sample outside the blood vessel. For example, a low dose of heparin in a solution of saline may be used as the anti-coagulant solution in the present invention. Other anti-coagulant agents that may be used, include, but are not limited to Warfarin and Coumadin.

Optionally, fluid container 9 may be a regular infusion bag, such as but not limited to, a saline-filled bag, administered to patient 2. Thus, automated blood analysis device 1 also performs the task of regulating the infusion by controlling the rate of pump 11. In this optional case, stopcock 17 is not needed in the design, and automated blood analysis device 1 acts as an integrated infusion and blood analysis device.

Figure 2A:
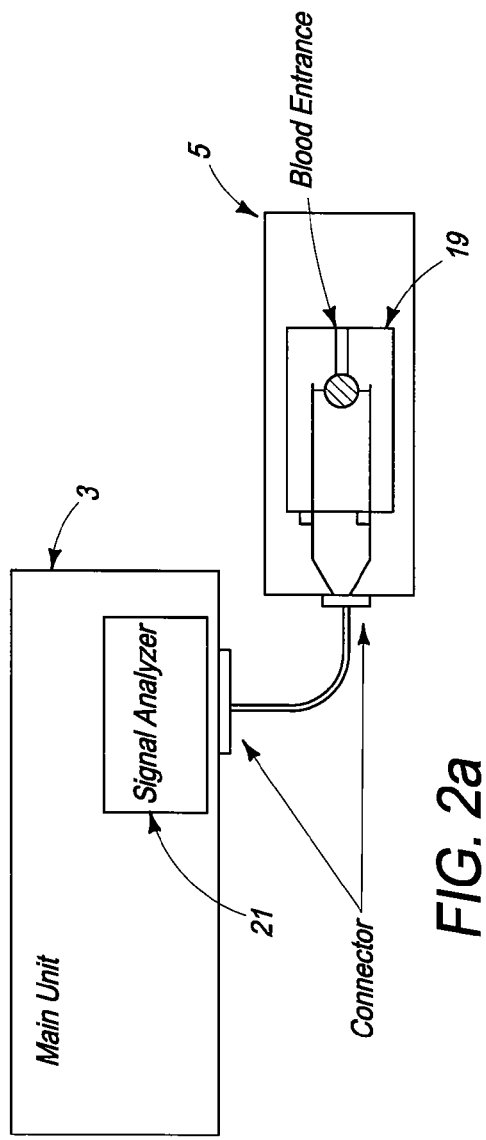
FIG. 2a schematically illustrates a first embodiment of a signal analyzer and a sensor used with the automated blood analysis device of the present invention.

FIG. 2a schematically illustrates a first preferred embodiment of a signal analyzer and a sensor used with the automated blood analysis device of the present invention. In this preferred embodiment, sensor 19 is preferably a single use electrochemical sensor capable of detecting the presence and/or measuring the level of an analyte in a blood sample via electrochemical oxidation and reduction reactions at the sensor. Electrochemical sensor 19 provides electrical input signal(s) to a signal analyzer 21, which converts these signal(s) to a correlated usable output, which can be, but is not limited to, an amount, concentration, or level of an analyte, such as glucose, in the patient blood sample. Main unit 3 ensures that electrochemical sensor 19 is maintained in direct contact with the blood sample until the electrical input signals reach a steady state condition, and signal analyzer 21 measures the required blood analyte(s) and blood parameter(s). The required time period for sensor 19 to be in contact with a blood sample in order to enable the measurement is on the order of seconds (or less).

In a preferred embodiment the electrochemical sensor 19 comprises both a working and a counter enzyme electrode. A counter electrode refers to an electrode paired with the working enzyme electrode. A current equal in magnitude and opposite in sign to the current passing through the working electrode passes through the counter electrode. As used in the present invention, the counter electrode also includes those electrodes which function as reference electrodes (i.e., a counter electrode and a reference electrode may refer to the same electrode and are used interchangeably).

Electrochemical sensors 19 are provided in suitable form for obtaining the desired blood chemistry measurements. In one preferred embodiment of the present invention, the blood glucose level is measured. Referring back to FIG. 2a, electrochemical sensors 19 as used for measuring blood glucose level preferably comprise the same type (but not limited to such type) as the sensors currently used in finger sticks for glucose measurement. In this case, single use sensor 19 provides electrical potentials having a magnitude representing concentration of glucose in the blood.

Figure 2B:
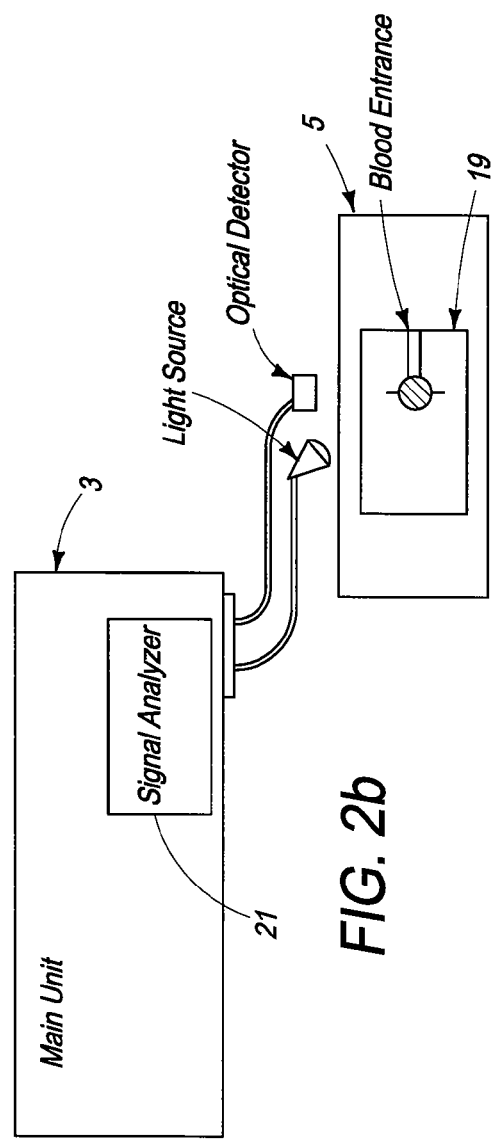
FIG. 2b schematically illustrates a second embodiment of a signal analyzer and a sensor used with the automated blood analysis device of the present invention.

FIG. 2b schematically illustrates a second preferred embodiment of a signal analyzer and a sensor used with the automated blood analysis device of the present invention. In this preferred embodiment, sensor 19 is preferably a single use optochemical sensor capable of detecting the presence and/or enabling measurement of the level of an analyte in a blood/plasma sample via optochemical oxidation and reduction reactions at the sensor.

For example, when using enzymatic reactions to measure a blood analyte, a component is added to the enzymes, which results in an optically measurable color change as a product of the reaction. Either an optical detector or a combination of a light source and an optical detector are used for measuring the blood analyte by measuring the color, and more particularly, color change, at the sensor.

In a third preferred embodiment (not shown) sensor 19 may optionally be a surface or miniature container, such as but not limited to a capillary tube, enabling storage of the blood sample for optical measurements. In this embodiment, both a light source and a light detector are used for measuring the blood analyte based on reflected, transmitted or other known optical effects such as Raman Spectroscopy, NIR or IR Spectroscopy, FTIR or fluoroscopy.

Various methods are available for packaging sensors 19 and are described in further detail below. Packaging options preferably include, but are not limited to: embedding a plurality of sensors 19 in a multi-layered tape structure encapsulated in a compact cassette formation; attaching a plurality of sensors 19 to a tape; or packaging a plurality of sensors 19 in a drum that enables singular selection of a sensor 19.

Figure 3A:
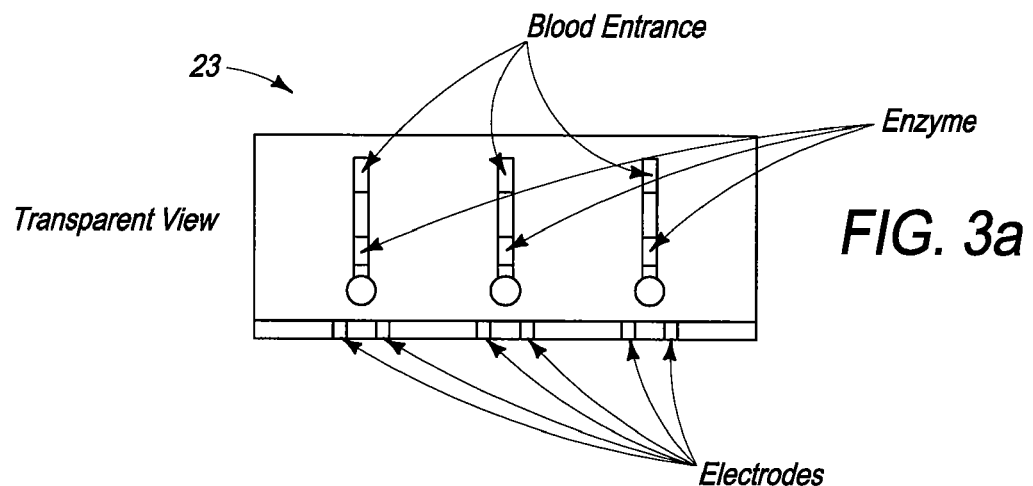
FIGS. 3a-3d illustrate a sensor tape, as used in FIGS. 1a-1e and 2a-2b as a multiple-layer element in a first arrangement.
Figure 3B:
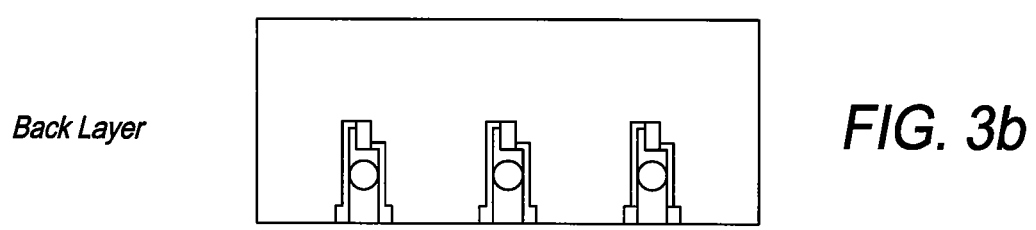
Figure 3C:
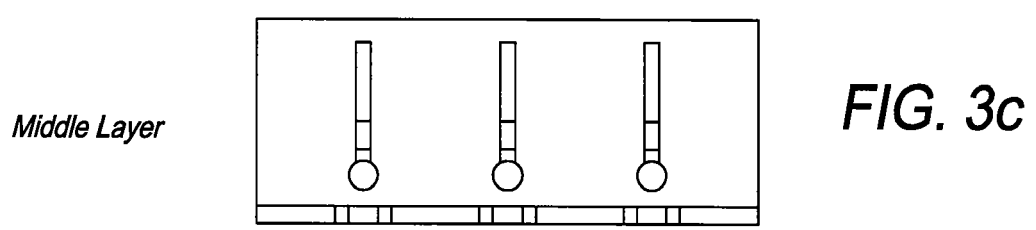
Figure 3D:
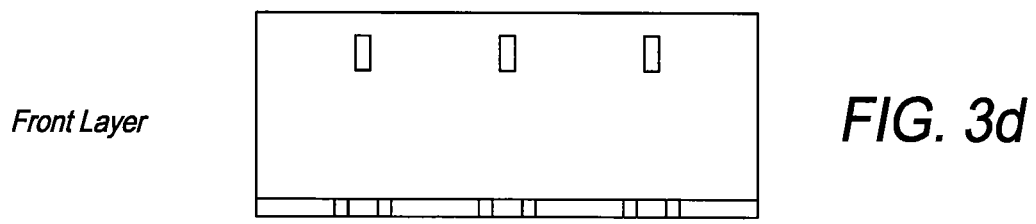

FIGS. 3a, 3b, 3c, and 3d illustrate a sensor tape, as used in FIGS. 1a-1e (not shown) and 2a-2b (not shown) as a multiple-layer element in a first preferred arrangement. FIG. 3a illustrates a transparent view of the multi-layer sensor tape 23 as used in a preferred embodiment of the present invention, and described in further detail below. FIG. 3b depicts the back layer of the sensor tape 23 as used in a preferred embodiment of the present invention, and described in further detail below. FIG. 3c illustrates the middle layer of the sensor tape 23 as used in a preferred embodiment of the present invention, and described in further detail below. FIG. 3d illustrates the front layer of the sensor tape 23 as used in a preferred embodiment of the present invention, and described in further detail below. Sensor tape 23 preferably comprises at least one sensor 19, and even more preferably comprises a plurality of sensors 19.

The preferred arrangement of sensor tape 23 comprises a front layer (shown in FIG. 3d) that defines at least one rectangular hole capable of being placed in contact with a corresponding hole in the infusion tube; a middle layer (shown in FIG. 3c), substantially coplanar with the front layer, that is capable of transporting a blood sample by means of at least one capillary channel and further includes a suitable enzyme coating; and a back layer (shown in FIG. 3b), underlying the middle transporting layer, that comprises a plurality of electrochemical sensor electrodes 19 for sensing required blood analytes such as, but not limited to glucose. Positioned at one end of the at least one capillary channel in the middle transport layer is a hole provided for an air outlet.

The front layer of sensor tape 23, and thus each sensor 19, may optionally be coated with a membrane for blocking the enzyme layer. When using a membrane coating to block the enzyme layer, sensor 19 measures the plasma analyte level, such as plasma glucose level instead of the blood analyte level. To measure the whole blood glucose level the reagents at the sensor need to cause the red blood cells (RBC) to explode via hemolysis of the blood at the capillary near the sensor. In measuring the whole blood glucose level via hemolysis, the resulting lysate cannot be returned into the blood stream, and thus, such method requires suitable isolation of the measured blood sample. Optionally, the membrane coating is placed inside sampling interface mechanism 18 for blocking the enzyme layer.

Figure 4A:
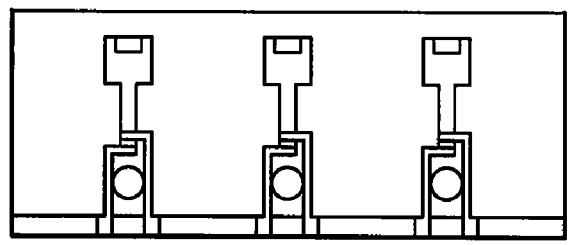
FIGS. 4a-4d illustrate a sensor tape, as used in FIGS. 1a-1e and 2a-2b as a multiple-layer element in a second arrangement.
Figure 4B:
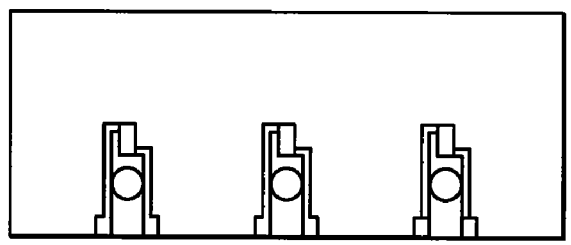
Figure 4C:
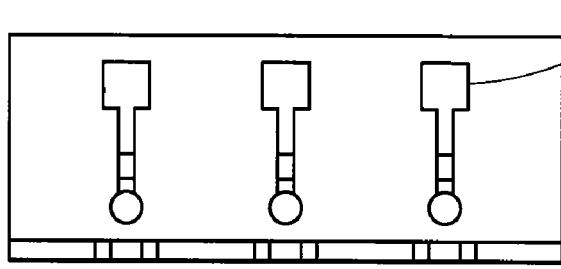
Figure 4D:
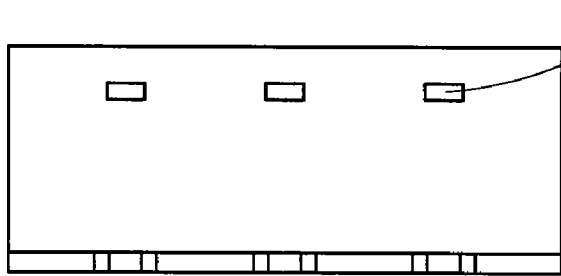

Now referring to FIGS. 4a, 4b, 4c, and 4d, a sensor tape, as used in FIGS. 1a-1e (not shown) and 2a-2b (not shown) as a multiple-layer element in a second preferred arrangement is illustrated. The multi-layer sensor tape of FIG. 4 further includes a square compartment 25 in middle layer 4c that effectively isolates blood for measurement. Particularly, FIG. 4c illustrates a preferred structural embodiment of the middle layer of sensor tape 23 wherein the blood first fills a square compartment 25 of the middle layer through the rectangular opening 26 at the top layer shown in FIG. 4d. After square compartment 25 is filled with blood, sensor tape 23 is advanced from a first position aligned with the sampling interface mechanism 18 (not shown) to a second position. At the shifted second position, the rectangular opening 26 at the top layer is exposed to air. Thus, the blood flows through the capillary channel to sensor 19 at a slower rate. At the other end of the capillary channel is an aperture 27 provided for an air outlet. Via this opening at the other end of the capillary tube, the blood that reacts with the enzyme and other reagents causing the hemolytic reaction is effectively isolated from the blood that is returned to the body.

As described with respect to FIGS. 1a-1e and FIGS. 2a-2b above, single use sensors 19 are preferably packaged into a disposable cassette 5 that is replaced periodically. Sensor cassette 5 is preferably sterile, and is also preferably disposed after use with a single patient 2. Sensor cassette 5 supports at least one or a plurality of single use sensors 19 that are advanced sequentially and positioned for direct contact with the drawn blood sample. After completing a measurement, the used sensor 19 is automatically advanced from the measurement location to a location for disposed sensors. Between measurements, the system moves a new sensor 19 forward, thus replacing the one used in the previous measurement. Various cassette sizes can be manufactured and sensor cassette 5 can be available, but is not limited to 25, 50, or 100 measurement capacities. In a preferred design, sensor cassette 5 also stores the consumed test supplies and sample waster. As shown in FIGS. 1a, 1b, 1d, and 1e, an external waste container 7 may optionally be used to store the waste fluid and/or consumed test supplies.

In addition, sensor cassette 5 may optionally include different types of single use sensors 19 in one cassette, wherein each sensor is capable of measuring a different type of blood analytes or blood parameters. In this case, sensor selection is made based upon either operator programming or selection before usage. In another optional embodiment, sensor cassette 5 may include a plurality of cassettes, each comprising a different type of sensor 19. The same automated blood sampling means is used for each measurement.

The use of single-use sensors 19 (similar to the use of finger stick sensors) eliminates the need for time-consuming operator-directed device calibration procedures. In particular, each sensor cassette 5 can be factory pre-calibrated. Optionally, sensor cassette 5 or plurality thereof and individual sensors 19 of the same type have the same pre-calibration values. Main display and control unit 3 can automatically read the cassette factory calibration values by standard means well-known to those of ordinary skill in the art, such as by reading the data from a barcode or an EPROM embedded in sensor cassette 5. Optionally, factory values may be entered manually.

In addition, sensor cassette 5 may be hermetically sealed and/or include humidity controls means, such as, but not limited to a small bag of dessicant material. In another option, each sensor 19 or a portion thereof, may be contained in a packaging that is automatically opened prior to measurement. Optionally, the measurement portion of the sensors 19 can be covered with a thin layer that protects the reagent area against moisture and/or light during storage (particularly useful for both electrochemical and optochemical sensors). The thin protective layer can be automatically peeled off by a peeling element (not shown), prior to the sensor being placed in position for measurement. The peeling element may comprise, but is not limited to, an edge-knife element strategically placed inside sensor cassette 5.

When using electrochemical sensors 19, sensor cassette 5 includes an electronic interface to main unit 3 of automated blood analysis device 1 and/or signal analyzer 21. When using optochemical or optical sensors 19, an electronic interface is optional, and sensor cassette 5 can be designed to work with only a mechanical interface to main unit 3 of automated blood analysis device 1. In another embodiment, sensor cassette 5 may optionally include a small battery power supply in case of power failure.

In a preferred embodiment, sensor cassette 5 may be either attached or inserted into main unit 3 of automated blood analysis device 1. In the alternative, main unit 3 may include an external sub-unit (not shown) that serves as the receiving interface for sensor cassette 5. Thus, sensor cassette 5 can be placed in proximity to patient 2 without limiting the size of main unit 3. In another embodiment, sensor cassette 5 may optionally be attached to main unit 3 of automated blood analysis device 1 by means of a data connector, an optional power connection means, and tubing.

Automated blood analysis device 1 may optionally include additional features and measurement mechanisms. As described briefly above, in one preferred option, automated blood analysis device 1 includes the capability of detecting whether blood has reached the proximity of sensor cassette 5 and/or the proximity of stopcock 17 via a blood optical sensor. Preferably, the method of detecting whether undiluted blood has reached the proximity of sensor cassette 5 and is ready for sampling is to illuminate the tubing in the proximity of sensor cassette 5. Based upon the transmitted and/or reflected signal, the device can establish whether the fluid in the specific segment is undiluted blood. The amount of withdrawn dead space is measured and the dead-space can also be managed by optically sensing the arrival and departure of blood from the line proximal to sensor cassette 5 and/or the proximity of stopcock 17.

In another option, automated blood analysis device 1 may include means for comparing the optical parameters of the fluid inside the tubing at least at two separate measurement points, wherein the at least one first measuring point is indicative of the fluid in the proximity of sensor cassette 5 or line 16 leading to sensor cassette 5 (when line 16 is used), and the second or last measuring point is a reference point where it can be safely estimated that the blood is undiluted. Preferably, this latter point is as close to the vascular access point as possible.

In another optional embodiment, automated blood analysis device 1 is capable of performing optical measurements on the blood sample or fluid proximate to sensor cassette 5. The automated blood analysis device 1 then combines optical measurements with electrochemical measurements of blood analytes. Thus, the potential inaccuracies in the measurement of a required blood parameter are corrected by combining the measurement of a blood parameter by means of a sensor 19 with optical measurements of other related blood parameters.

In an exemplary embodiment, the optically measured hematocrit level is used to correct for the influence of hemodilution on blood analytes such as, but not limited to, glucose. Preferably, hematocrit levels and hemoglobin oxygenation levels are accurately measured using three wavelengths. If for example, but not limited to such example, individual sensor 19 is a glucose test strip, the whole blood glucose level measured by sensor 19 is influenced by the hematocrit level. If the hematocrit level is high or low it may alter the results, owing to factors that are separate from yet compounded by the effects of different water distribution in the different blood components. The glucose reading is thus more accurate when the hemoglobin oxygenation and hematocrit levels are taken into account. By measuring the hemodilution, it also becomes possible to predict the distribution of glucose in different fluid compartments within the body, including, but not limited to, ECF and blood versus ICF parameters. Other combinations regarding the number and type of optical wavelengths and the parameters to be corrected can be used according to known correlations between blood parameters.

In still another optional embodiment, automated blood analysis device 1 performs independent optical measurements of the blood sample drawn in the infusion line in order to measure at least one blood parameter or at least one blood analyte, such as hemoglobin level. The blood sample inside the infusion line is illuminated at a plurality of discrete wavelengths selected from the near infrared (IR) spectrum. As it is readily known to persons of ordinary skill in the art, measurements of intensity of transmitted or reflected light at these wavelengths are taken, and an analysis of transmittance or reflectance ratios for various wavelengths is performed. In one preferred embodiment of the system, the glucose level is measured optically using several wavelengths, using illumination principles described in further detail below.

The illumination source can be a single, multi-wavelength laser diode, a tunable laser or a series of discrete LEDs or laser diode elements, each emitting a distinct wavelength of light selected from the near infrared region. Alternatively, the illumination source can be a broadband near infrared (IR) emitter, emitting wavelengths as part of a broadband interrogation burst of IR light or radiation, such as lamps used for spectroscopy. A plurality of detector arrays detect light reflected and/or transmitted by sample blood. The wavelength selection can be done by either sequencing single wavelength light sources or by wavelength selective elements, such as using different filters for the different detectors or using a grating that directs the different wavelengths to the different detectors. The detector array converts the reflected light into electrical signals indicative of the degree of absorption light at each wavelength and transfers the converted signals to an absorption ratio analyzer such as microprocessor 32 of main unit 3. The analyzer processes the electrical signals and derives an absorption (e.g., a reflection and/or transmittance) ratio for at least two of the wavelengths. The analyzer then compares the calculated ratio with predetermined values to detect the concentration and/or presence of an analyte such as, but not limited to glucose, hematocrit levels and/or hemoglobin oxygenation levels in the patient blood sample. For example, changes in the ratios can be correlated with the specific near infrared (IR) absorption peak for glucose at about 1650 nm or 2000-2500 nm or around 10 micron, which varies with concentration of the blood analyte.

Figure 5A:
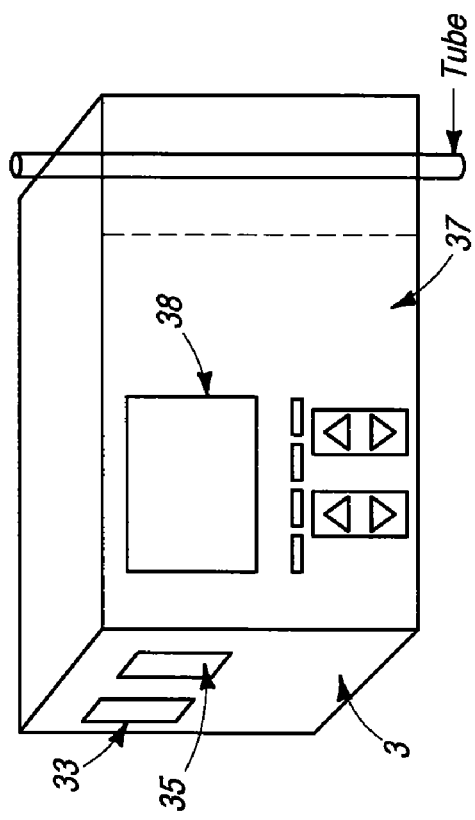
FIGS. 5a and 5b illustrate the functional elements of and operational implementation of the main unit of an automated blood analysis device.
Figure 5B:
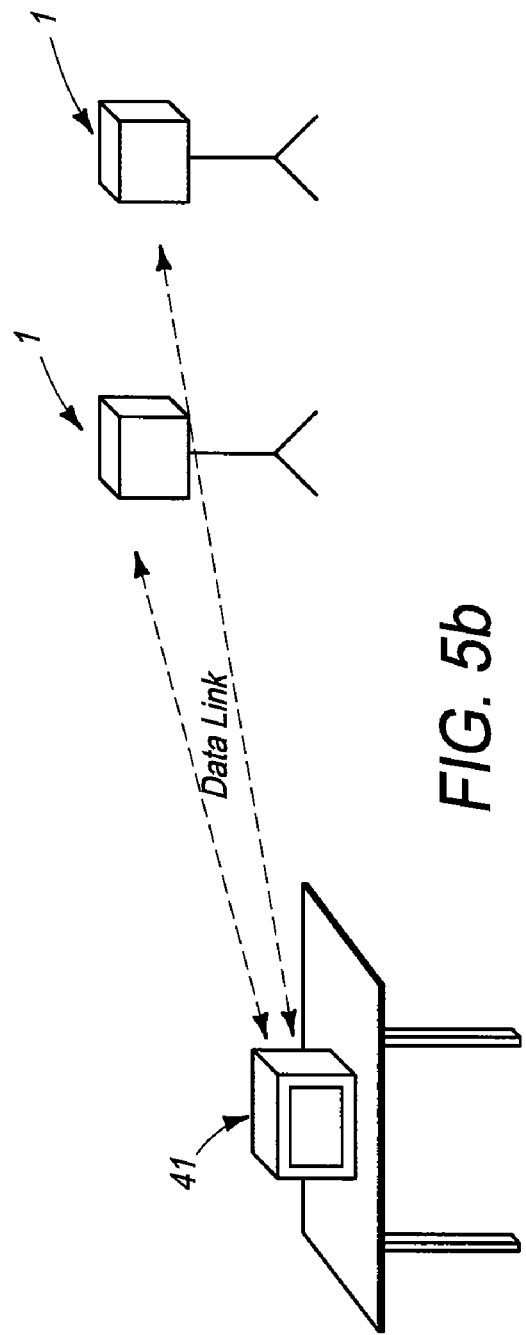

FIGS. 5*a* and 5*b* illustrate the functional elements of and operational implementation of main control unit 3 (also referred to as "main unit") of an automated blood analysis device 1 in several settings, including a clinical setting. Now referring to FIG. 5*a*, the functional elements of the main control unit 3 of an automated blood analysis device 1 are shown. Automated blood analysis device 1 is programmed to operate via main control unit 3, enabling the automated blood sampling and analysis at predetermined intervals or time periods. For example, but not limited to such example, the operator can opt for automated measurements of blood analytes (based on automated blood samples) as frequently as every fifteen minutes. Shorter time periods, as short as one minute, are also possible. Main unit 3 displays test results as early as thirty seconds after the blood sample reaches the sensor tape. Measurement results are stored in a device memory 31 for trending or later download.

Main unit 3 comprises a general purpose programmable microprocessor unit 32 (not shown), as are well known to persons of ordinary skill in the art; an internal communication link 33; an external communication link 35; a panel 37 including a display 38 and various user interfaces; and an optional battery 39. Preferably, signal analyzer 21, pump 11, and optional pump 13 are embedded in one unit with main unit 3. Main unit 3 can be manufactured in one unit or in several separate sub-units to fit operational and physical requirements.

Internal communication link 33 creates an electrical communication connection between main unit 3 to sensor cassette 5, three-way stopcock 17, pump 11, and signal analyzer 21 if pump 11 and signal analyzer 21 are not embedded in main unit 3. Thus, internal communication link 33 connects main unit 3 to sensor cassette 5 and any other electronic or electromechanical component of automated blood analysis device 1. Internal communication link 33 may be wired and/or wireless. Internal communication link 33 may also be based on a digital data link and/or on analog signals.

Internal communication link 33 enables main unit 3 to control, synchronize, and check the proper automated operation of the automated blood analysis device 1. Particularly, main unit 3 also includes required alert and built-in test capabilities. For example, pump 11 and main unit 3 can include all alert features required from infusion pumps such as detection of air in the line or detection of a blocked tube. Main unit 3 also enables the user to define a goal value or a goal range for the blood parameters measured by automated blood analysis device 1. Thus, if a measurement is above or below the defined range or value, main unit 3 issues an alert to the user in audio and/or visible form, through wired or wireless means.

External communication link 35 may optionally include interfaces to external devices such as, but not limited to, printers, hospital data network(s), external processors and display units, other monitoring devices, and/or devices used for infusing substances in the patient. The connection between main unit 3 and the various possible external units can be made via any of the known wired or wireless communication methods, as are well-known in the art.

Optionally, main unit 3 can control the operation of an external infusion pump that uses the same vascular access point for infusion as automated blood analysis device 1. In this scenario, main unit 3 issues suitable command signals to the external infusion pump to defuse alarms while halting infusion during blood sampling and measurement. In addition, main unit 3 ensures automatic restart of the external infusion pump after the blood sample has been taken. As will be readily apparent to those skilled in the art, the external infusion pump includes an appropriate data interface for receiving and interpreting the command signals. Thus, automated blood analysis device 1 acts as an integrated fluid infusion and blood analysis device.

Optionally, automated blood analysis device 1 can provide feedback to an external infusion device in order to regulate the amount and rate of infusing fluid substances into the patient. Optionally, main unit 3 can also control the external infusion device, thus integrating the automatic measurement and the external infusion device into one system. In an integrated set-up, main unit 3 automatically supports adaptive algorithms for adjustment of rate and volume of substances to be infused according to the measurements. In addition, look-up tables and algorithms based on a measurement history and/or required future trend are also supported. The integrated system also supports infusion of bolus volumes combined with continuous infusion. In addition, it is possible to infuse several separate substances in parallel and in correlation according to a required algorithm. For example, main unit 3 controls and regulates the rate and volume of an infusion of IV insulin in parallel with infusion of a dextrose solution.

As shown in FIG. 5b, automated blood analysis device 1 may optionally be connected to an integrated monitor 41 which includes both display and human interface means. Integrated monitor 41 can be placed proximate to a central counter where at least part of the medical staff is located. In addition, integrated monitor 41 is connected by wired or wireless links to one or more automated devices for blood analysis 1. Thus, one operator can control and check the operation of several devices without requiring physical presence at the site of the device. In another embodiment, data from automated blood analysis device 1 can be displayed alongside other parameters and/or vital signs. Optionally, data from data from automated blood analysis device 1 may be correlated and analyzed with other blood parameters and/or vital signals in order to indicate the overall patient condition and/or to indicate critical conditions that require intervention. In one embodiment, main unit 3 performs this data analysis and/or data correlation. Main unit 3 also facilitates data retrieval and archiving as may be required.

Figure 6A:
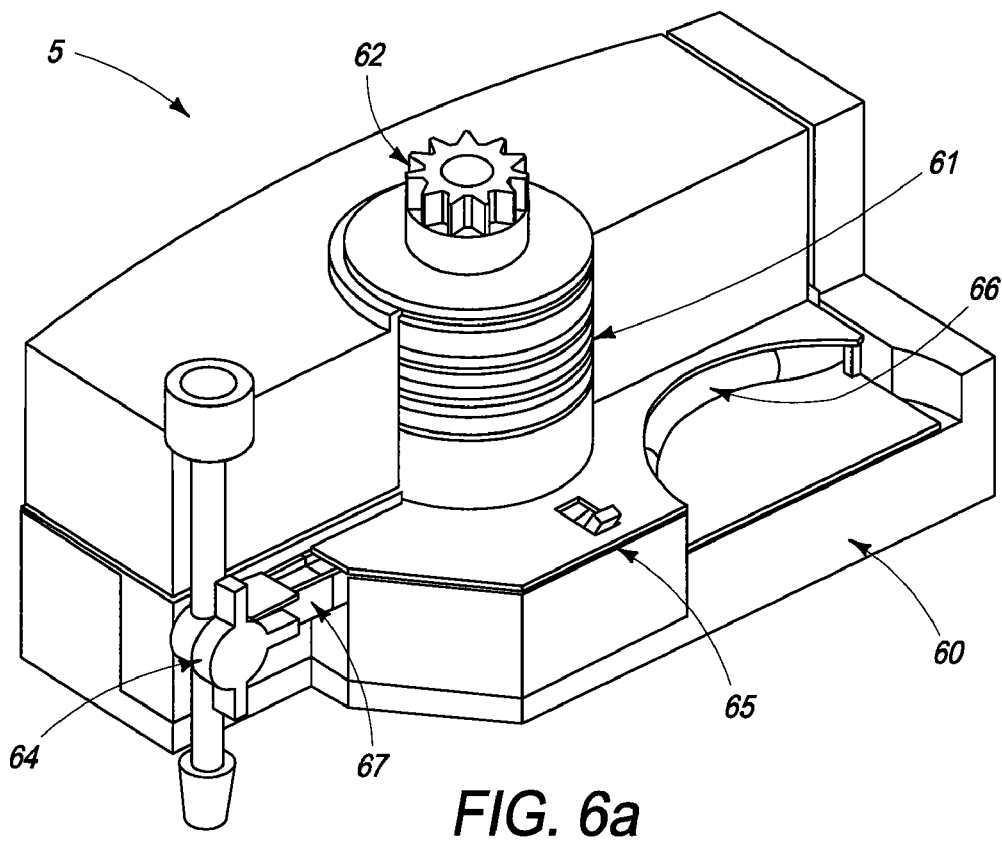
FIG. 6a is an illustration of a sensor cassette as used in the automated blood analysis device of the present invention.

FIG. 6a is an illustration of a preferred sensor cassette as used in the automated blood analysis device 1 of the present invention. Sensor cassette 5 is preferably made of plastic and has a clamshell-type structure. In one preferred embodiment, but not limited to such embodiment, sensor cassette 5 includes at least 50 single-use sensors 19. In another preferred embodiment, sensor 19 is a glucose test strip.

An optional fluid trap 60 is located on the bottom of sensor cassette 5. The lower panel of fluid trap 60 is sealed to minimize fluid spill. When used, fluid trap 60 is optionally shaped to fill the outline of sensor cassette 5 and has a volume large enough to contain extra blood samples and other potential fluids (such as purging fluid) not used for the measurements. Sensor cassette 5 also includes a drum 61 with a contact area (not shown) through which blood samples are taken inside sensor cassette 5. Drum 61 also includes a gear drive 62 enabling the rotation of sensors 19 into position, such that they face the contact area (not shown) during blood sample testing.

Figure 6B:
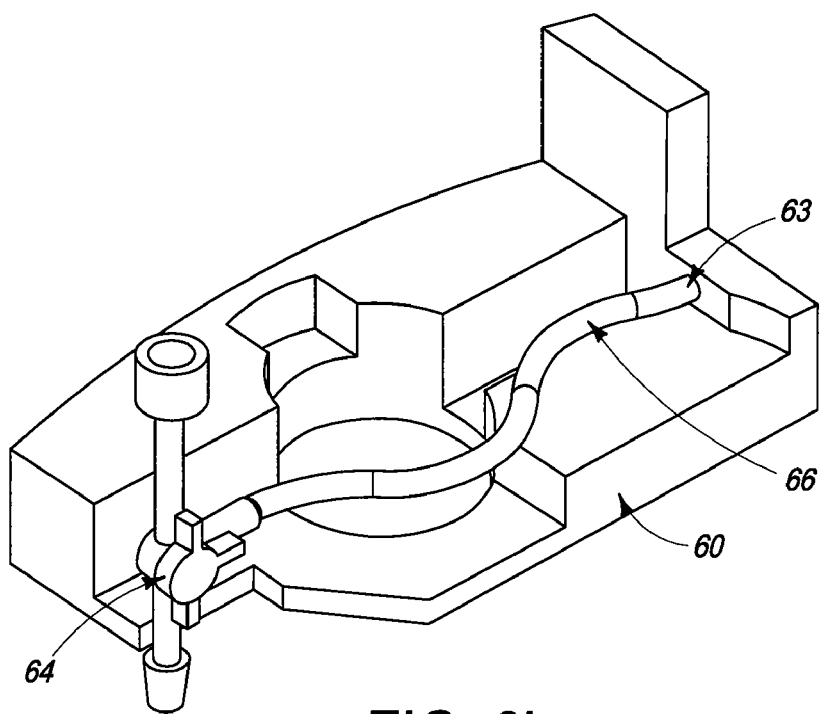

FIG. 6b is an internal view of the fluid handling mechanism of the preferred sensor cassette 5 of the present invention as depicted in FIG. 6a. Reference will also be made to FIG. 6a where necessary. The blood sampling mechanism includes internal tubing 63 for fluid flow and delivery; a three-way stopcock 64 to control the flow through internal tubing 63; and an actuator 65 (shown in FIG. 6a) that is positioned adjacent to internal tubing 63 opposite to the contact area (not shown), and serves to bend internal tubing 203 so that a blood sample may be driven inside sensor cassette 5 through the contact area. Internal tubing 63 also contains blood sample area 66. As discussed in greater detail below with reference to FIG. 6g, an alcohol wipe is provided to clean the tubing after each blood sample is measured and is refreshed between cleanings with a drip reservoir.

Referring back to FIG. 6a, additional optional features related to the design of sensor cassette 5 and automated blood analysis device 1 are described. An optical sensor (not shown) measures fluid parameters, such as hemoglobin level hematocrit level, and blood oxygen saturation, in the internal tubing 63 through an opening 67 positioned close to stopcock 64 to ensure that the sampled fluid includes undiluted blood, and in order to correct potential measurement errors made by sensor 19 due to changes in the hematocrit level of the blood sample.

Figure 6C:
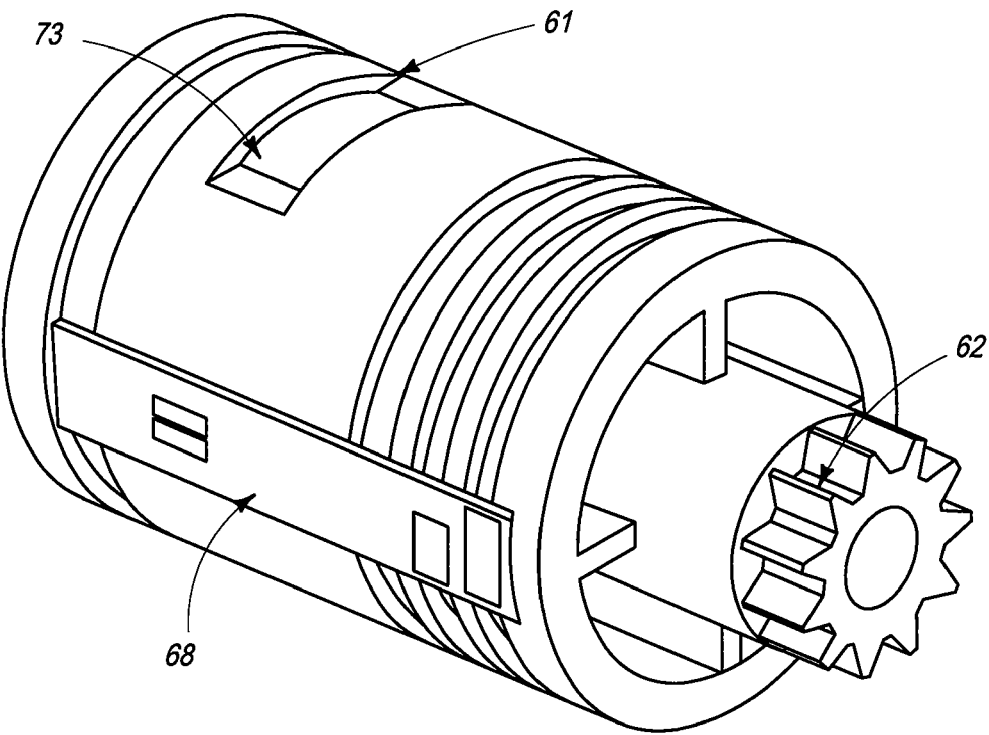
FIG. 6c is an isolated and expanded illustration of the drum structure of a sensor cassette as used in the automated blood analysis device of the present invention.

FIG. 6c is an isolated and expanded illustration of the drum structure of the preferred sensor cassette 5 as used in the automated blood analysis device of the present invention. Gear drive 62 is used to move drum 61 and thus advance test strips from test strip carrier area 68 to contact area (not shown). The sensor is advanced via advancement means, which include, but are not limited to mechanical, electrical, and/or optical devices for ensuring that sensor 19 is in position for measurement. For example, when closed, an electronic circuit indicates that sensor 19 is in position. In this preferred embodiment, and as generally required by electrochemical glucose test strips, electrical contact is made between the electrodes of sensor 19 and signal analyzer 21 prior to measurement.

Figure 6D:
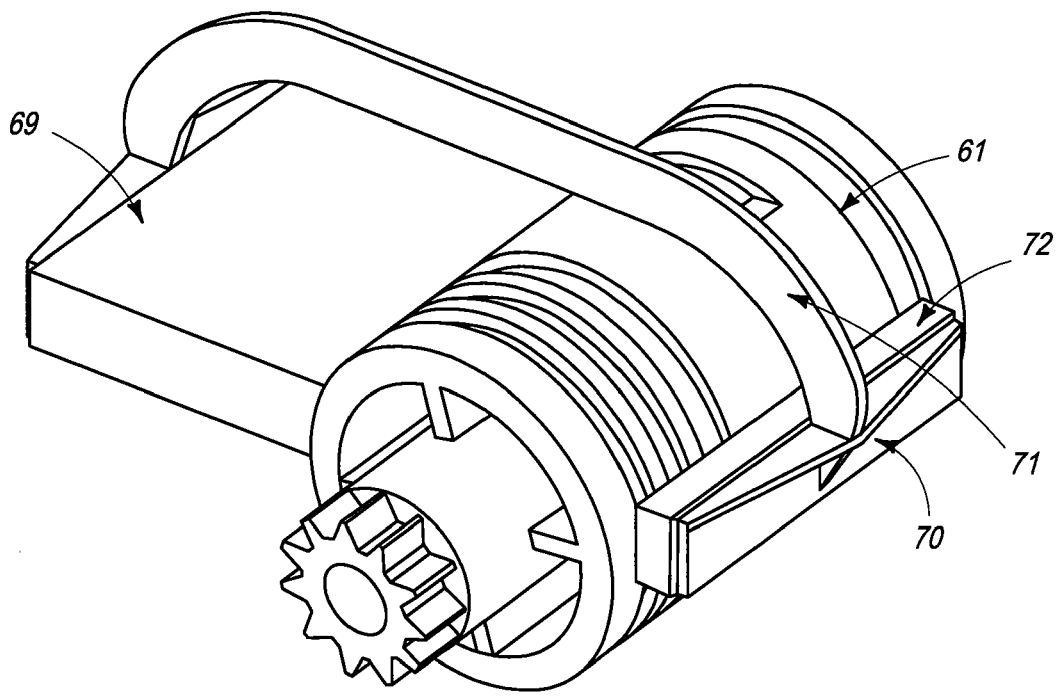
FIG. 6d is an isolated illustration of the test strip handling mechanism of the sensor cassette as used in the automated blood analysis device of the present invention.

FIG. 6d is an isolated illustration of the test strip handling mechanism of the preferred sensor cassette 5 as used in the automated blood analysis device of the present invention. Preferably, the test strip handling mechanism of the present invention contains a set of fifty clean test strips 69 placed into spring 70. Spring 70 has an arm 71 which wraps around one side of drum 61, thus keeping the test strips fastened up against the drum 61. Used test strips 72 are deposited on the opposite side of the drum as clean test strips 69.

Figure 6E:
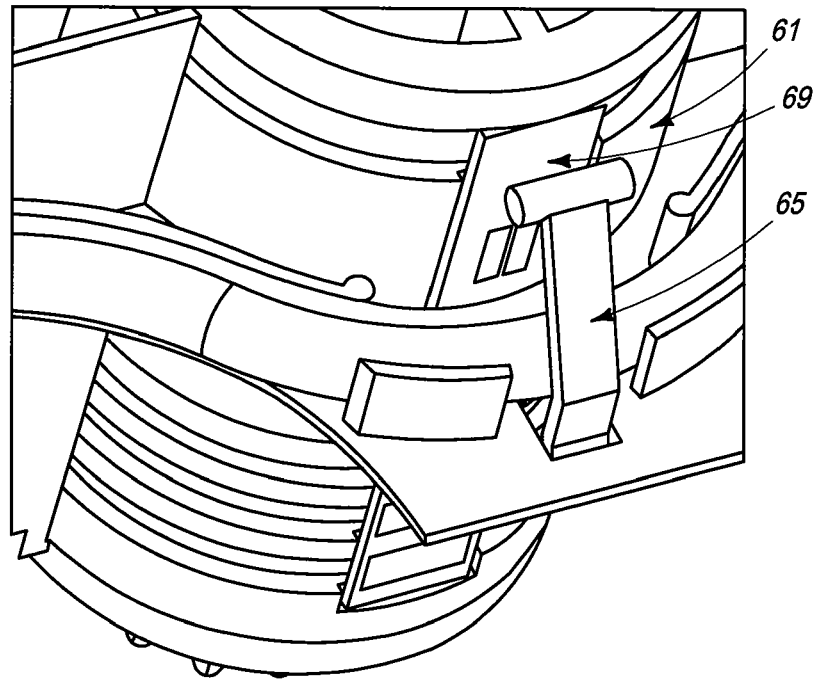
FIGS. 6e and 6f are expanded illustrations of the blood sample delivery operation as used in the as used in the automated blood analysis device of the present invention.
Figure 6F:
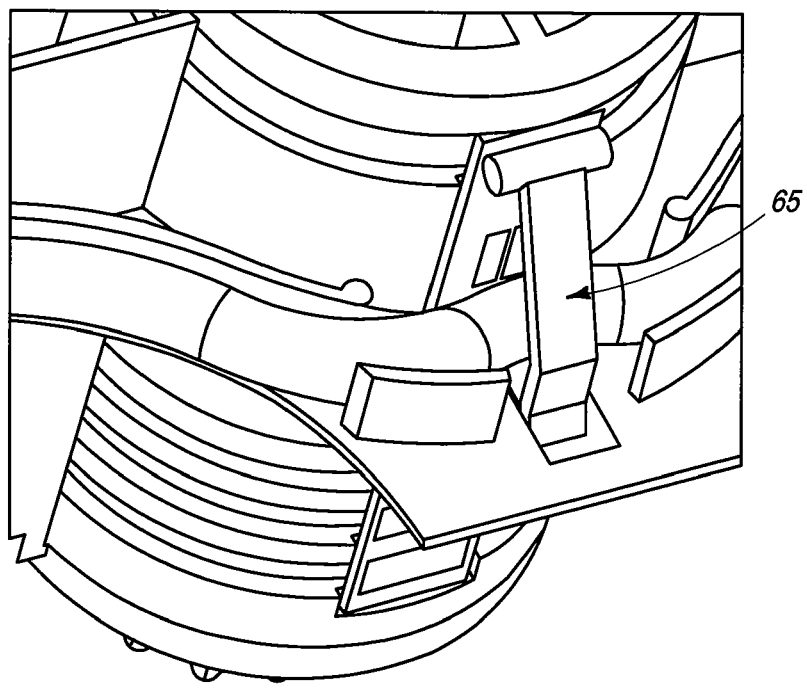

FIGS. 6e and 6f are expanded illustrations of the blood sample delivery operation as used in the automated blood analysis device of the present invention. Reference will now be made to either figure where appropriate. As shown in FIG. 6e, drum 61 is rotated until the test strip 69 meets electrical contacts (not shown, but located behind the test strip) and is in position, sensed by connecting pins P1 and P2 (not shown). The three way stopcock (not shown), described with reference to FIG. 6b above, is rotated into the proper position to retrieve a blood sample from the patient. The blood pumping operation is then started. The optical sensor, also described with reference to FIG. 2b above, indicates when blood is available in the sample area. The blood pump is then stopped. The three way stopcock is rotated back to the "IV to patient" position indicating that tube will deliver fluid to the patient intravenously. The actuator/tube bender 65, as shown in FIG. 6f, is actuated to press the tube against the test strip. The blood pump is "backed up" until the test strip registers the blood sample and the tubing is returned to its original position.

Figure 6G:
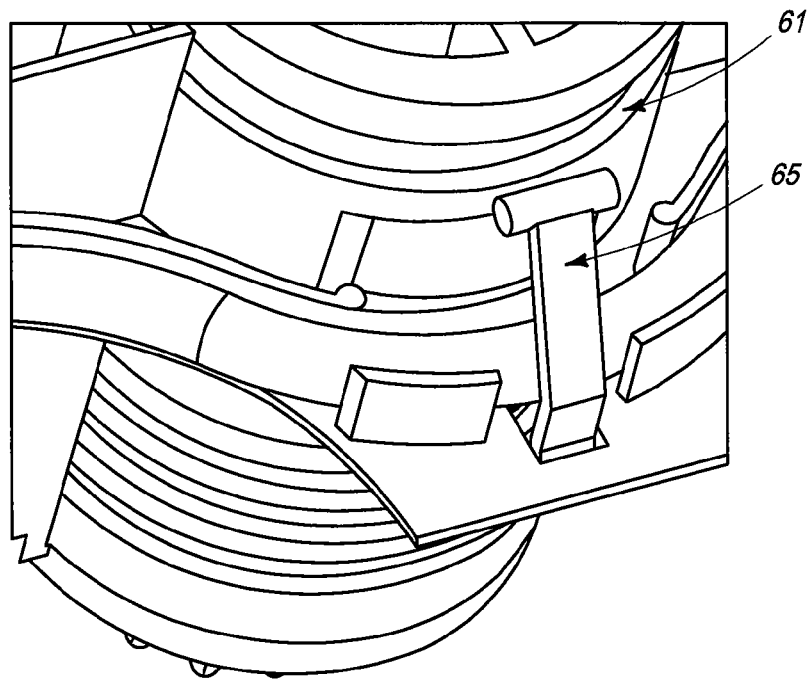
FIGS. 6g and 6h are illustrations of the tubing cleaning operation as used in the automated blood analysis device of the present invention.
Figure 6H:
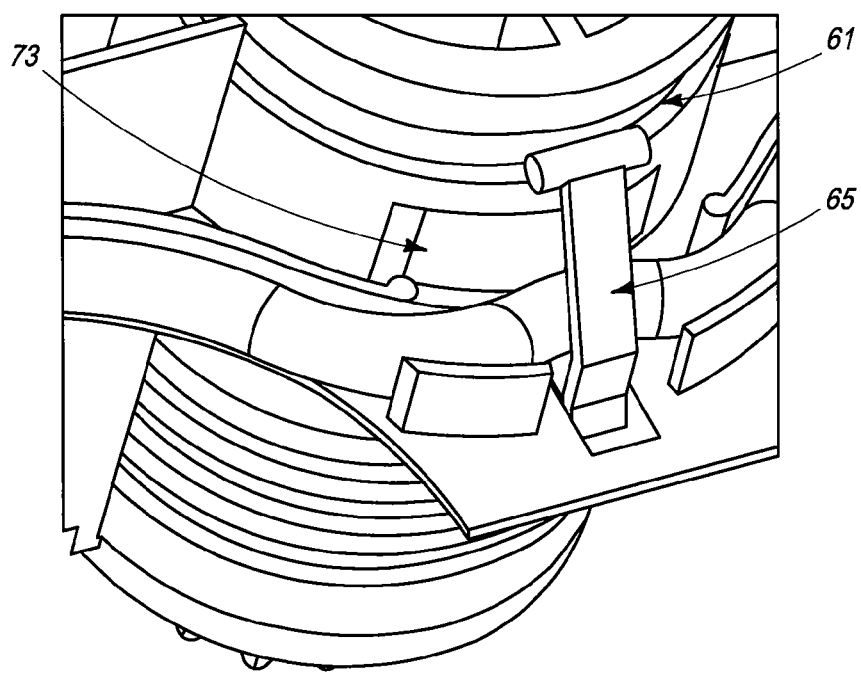

FIGS. 6g and 6h are illustrations of the tubing cleaning operation as used in the automated blood analysis device of the present invention. The three way stopcock (not shown) is rotated to the "IV solution into cassette" position. The blood pump begins to clean out the tubing, or flush it, with IV solution. The optical sensor is used for conformation. The three way stopcock is rotated back to "IV to patient" position. The drum 61 is rotated to dispose of the used test strip and position the alcohol wipe 73 (also shown in FIG. 2c). The alcohol wipe 73 is provided to clean the tubing after each blood sample is measured and is refreshed between cleanings with a drip reservoir. The tube bender/actuator 65 is bent, as shown in FIG. 6h to press the tube against the alcohol wipe, thus cleaning the tube. The drum 61 is then rotated back to its initial position.

Figure 7A:
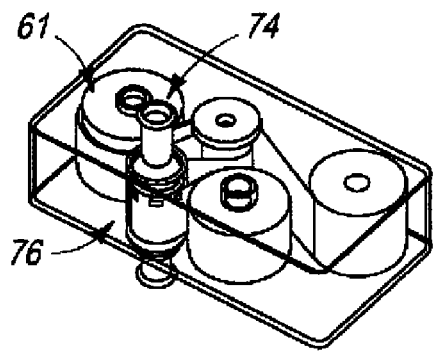
FIGS. 7a-7c depict a two-tape configuration of the sensor cassette used in connection with the automated blood analysis device of the present invention.
Figure 7B:
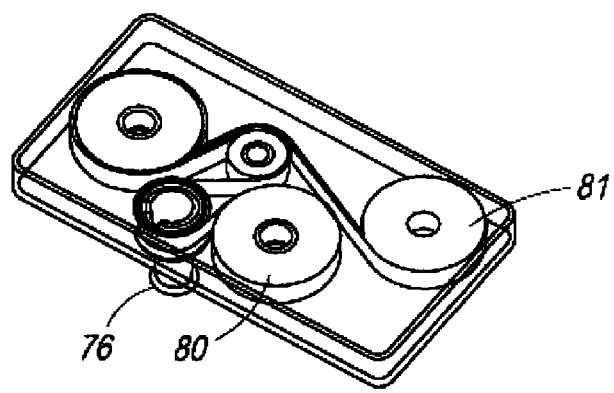
Figure 7C:
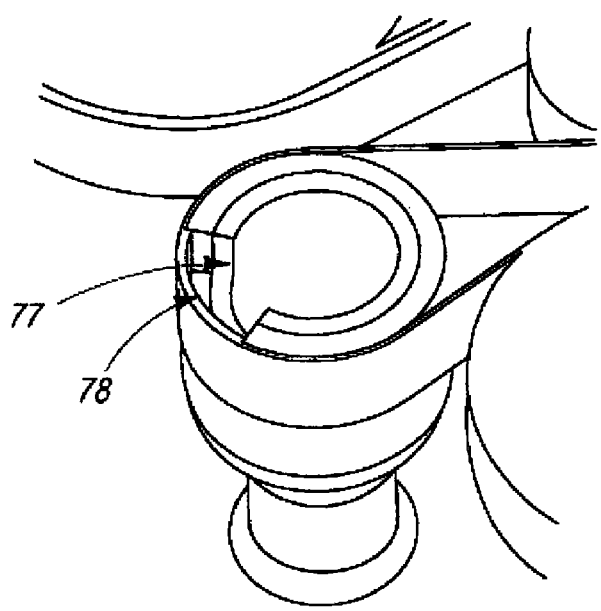
Figure 8:
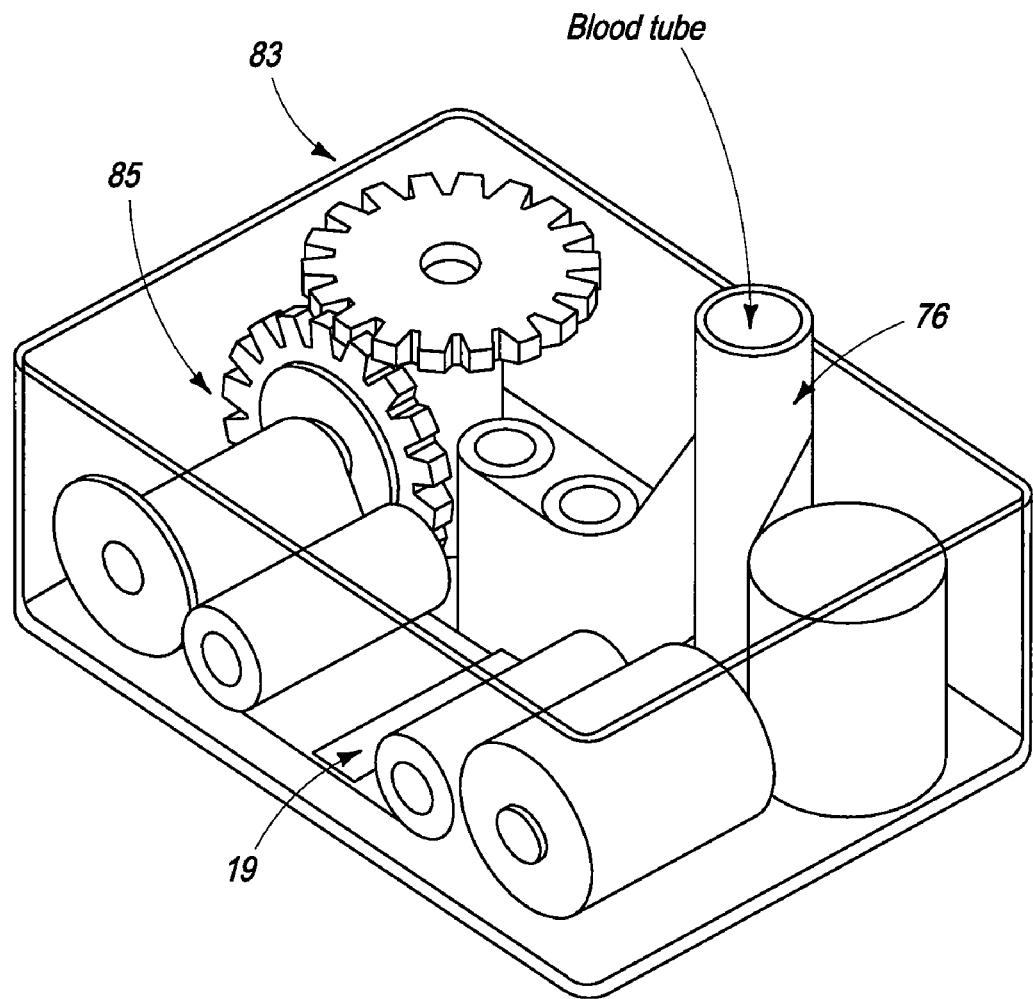
FIG. 8, depicts another embodiment for isolating measured blood, using glucose finger sticks attached onto a tape.

FIGS. 7a, 7b, 7c and 8 depict exemplary embodiments of sensor tape structures or sampling interface mechanisms that effectively isolate blood for measurement. More specifically, FIGS. 7a, 7b, and 7c depict a two-tape configuration of the sensor cassette used in connection with the automated blood analysis device of the present invention. The sensor cassette configuration of FIG. 8 is similar to that described in FIGS. 7a, 7b, and 7c, however, uses glucose finger sticks attached onto a tape.

Referring now to FIGS. 7a, 7b, and 7c an internal tube 74 passes through cylindrical element 76, which rotates around the internal tube. Internal tube 74 includes an opening 77 that is matched by window 78 in cylindrical element 76 each time a new blood sample is required for a new measurement. In this particular embodiment, sensor cassette 5 also includes a first tape 80 that further includes a set of capillaries. When the cylindrical element 76 is rotated and window 78 is matched with opening 77, first tape 80 is rotated bringing a capillary in contact with the blood and a blood sample is retained in the capillary. Once blood is disposed on first tape 80, first tape 80 and second tape 81 are advanced until the capillary with the blood sample of first tape 80 touches a sensor 19 on second tape 81. The blood sample is then transferred from first tape 80 to sensor 19, enabling measurement of the required blood parameter. In this configuration the first tape 80, second tape 81, and the cylindrical element 76 are driven by the same gear that is connected to drum 61.

Referring now to FIG. 8, yet another preferred embodiment for isolating measured blood is depicted. The sensor cassette configuration of FIG. 8 is similar to that described in FIGS. 7a, 7b, and 7c, however, uses glucose finger sticks attached onto a tape. Sensors 19 on second tape 81 are replaced with common glucose finger sticks attached to the tape, as are well-known to those of ordinary skill in the art. This design includes a first drum 83 and a second drum 85 rotating together, and driven by the same gear as cylindrical element 76.

Figure 9A:
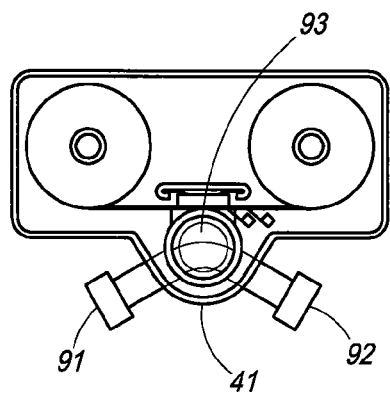
FIGS. 9a and 9b depict configurations of an external sealing valve used as part of the sampling interface mechanism in one embodiment of the automated blood analysis device of the present invention.
Figure 9A:
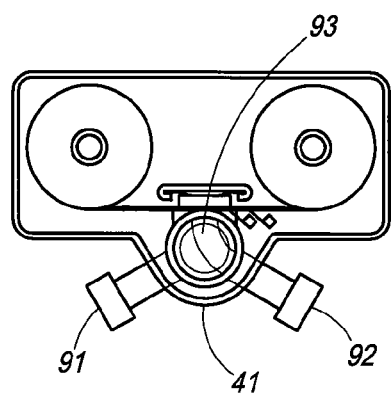
Figure 9B:
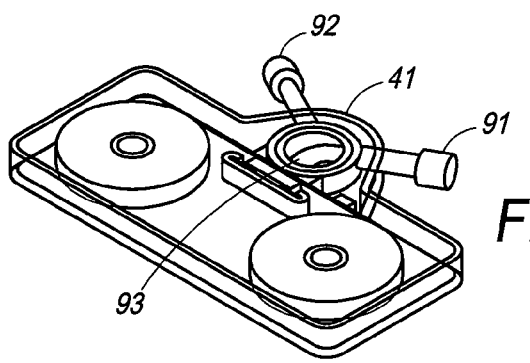
Figure 9B:
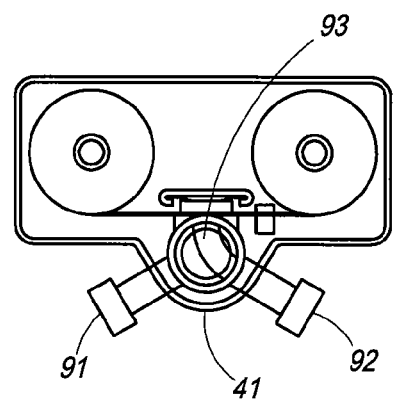

Alternative mechanisms for enabling sampling interface mechanism to withdraw the blood sample and bring it into contact with sensor 19 are now presented. FIGS. 9a and 9b depict configurations of an external sealing valve used as part of the sampling interface mechanism in one embodiment of the automated blood analysis device of the present invention. More specifically, FIGS. 9a and 9b illustrate yet another preferred embodiment depicting the use of an external valve to facilitate the sealing of the infusion tube with ease and convenience. The output ports 91 and 92 of external valve 41 are positioned at 120° angles from each other to enable self flushing of the valve inner tube 93.

Figure 9C:
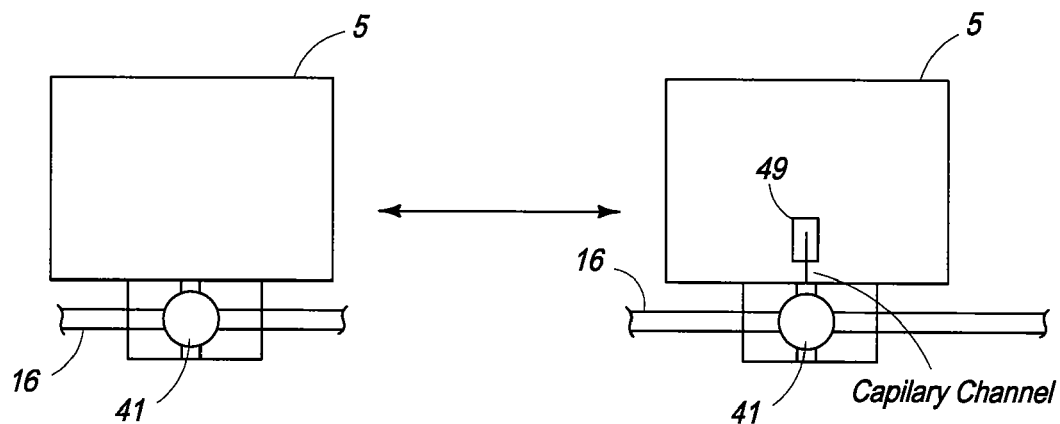
FIGS. 9c and 9d illustrate additional configurations of the external sealing valve used as part of the sampling interface mechanism in optional embodiments of the automated blood analysis device of the present invention.

FIG. 9c illustrates another configuration of an external sealing valve used as part of the sampling interface mechanism in one embodiment of the automated blood analysis device of the present invention. Sampling interface mechanism 18 (not shown) includes a valve 41. When blood reaches valve 41, valve 41 is automatically rotated 90°, thus bringing a blood sample inside sensor cassette 5. A capillary channel in sensor 19 is brought into contact with the blood sample inside valve 41, thus bringing a blood sample to the measurement area of sensor 19.

Figure 9D:
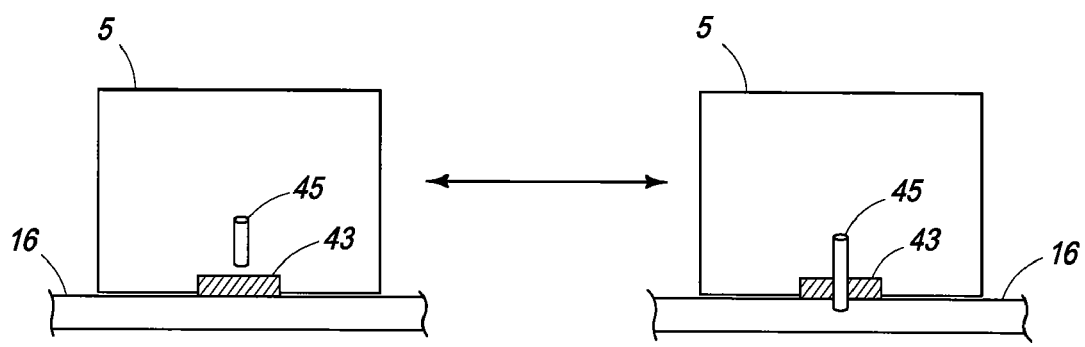

FIG. 9d illustrates another configuration of an external sealing valve used as part of the sampling interface mechanism in one embodiment of the automated blood analysis device of the present invention. Now referring to FIG. 9d, sampling interface mechanism 18 includes a membrane or valve 43 that separates sensor cassette 5 and the tube bringing the blood sample to sensor cassette 5 and at least one cannula 45. When the blood reaches the proximity of membrane or valve 43, cannula 45 is automatically advanced to penetrate valve 43 and reach the lumen of the tube. A blood sample is then taken and cannula 45 is retrieved inside sensor cassette 5 to bring the blood sample to sensor 19.

Figure 10A:
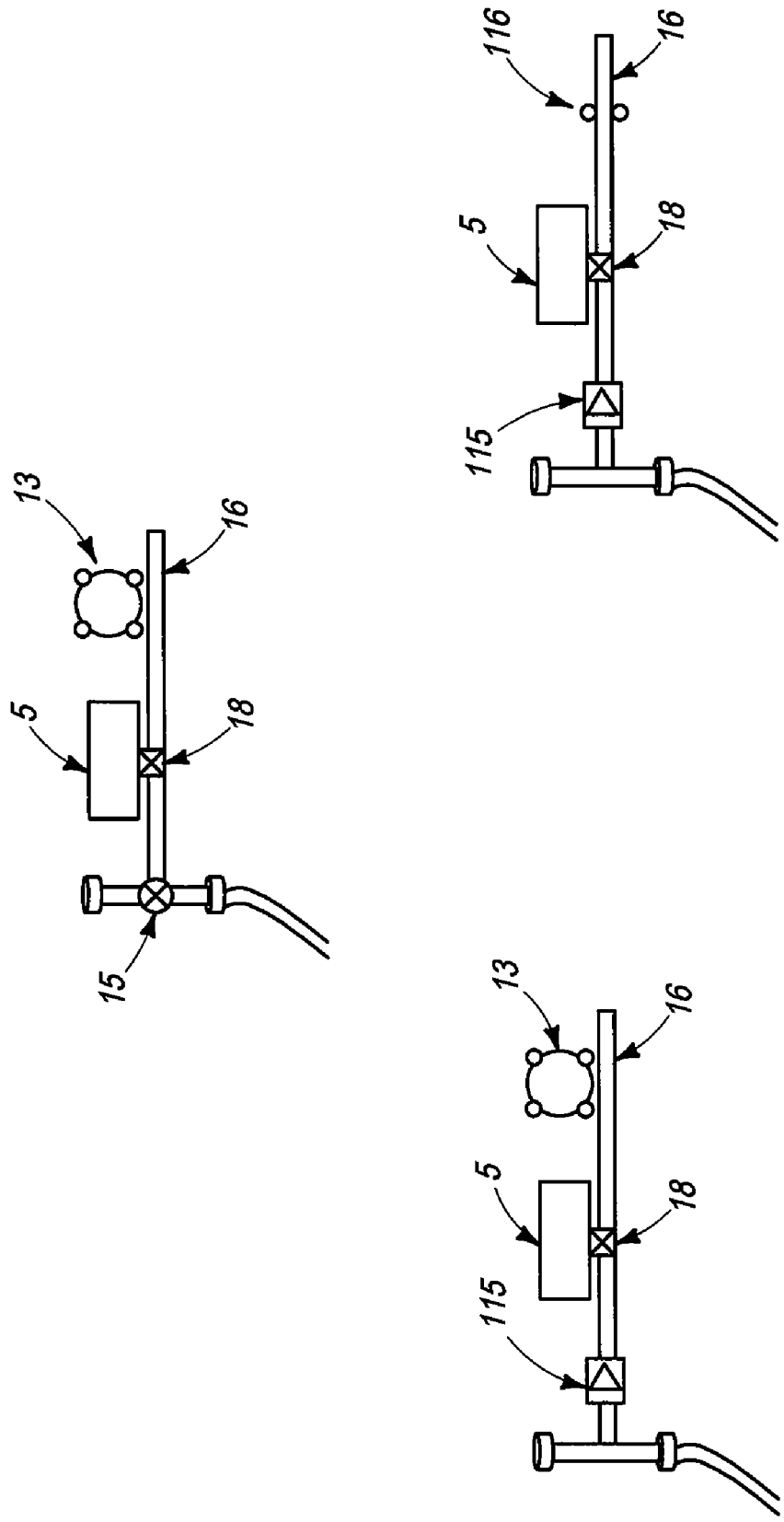
FIGS. 10a and 10b illustrate alternative methods for controlling the flow of fluids in connection to the automated blood analysis device of the present invention, as shown in FIGS. 1a, 1b, 1c, and 1d.
Figure 10B:
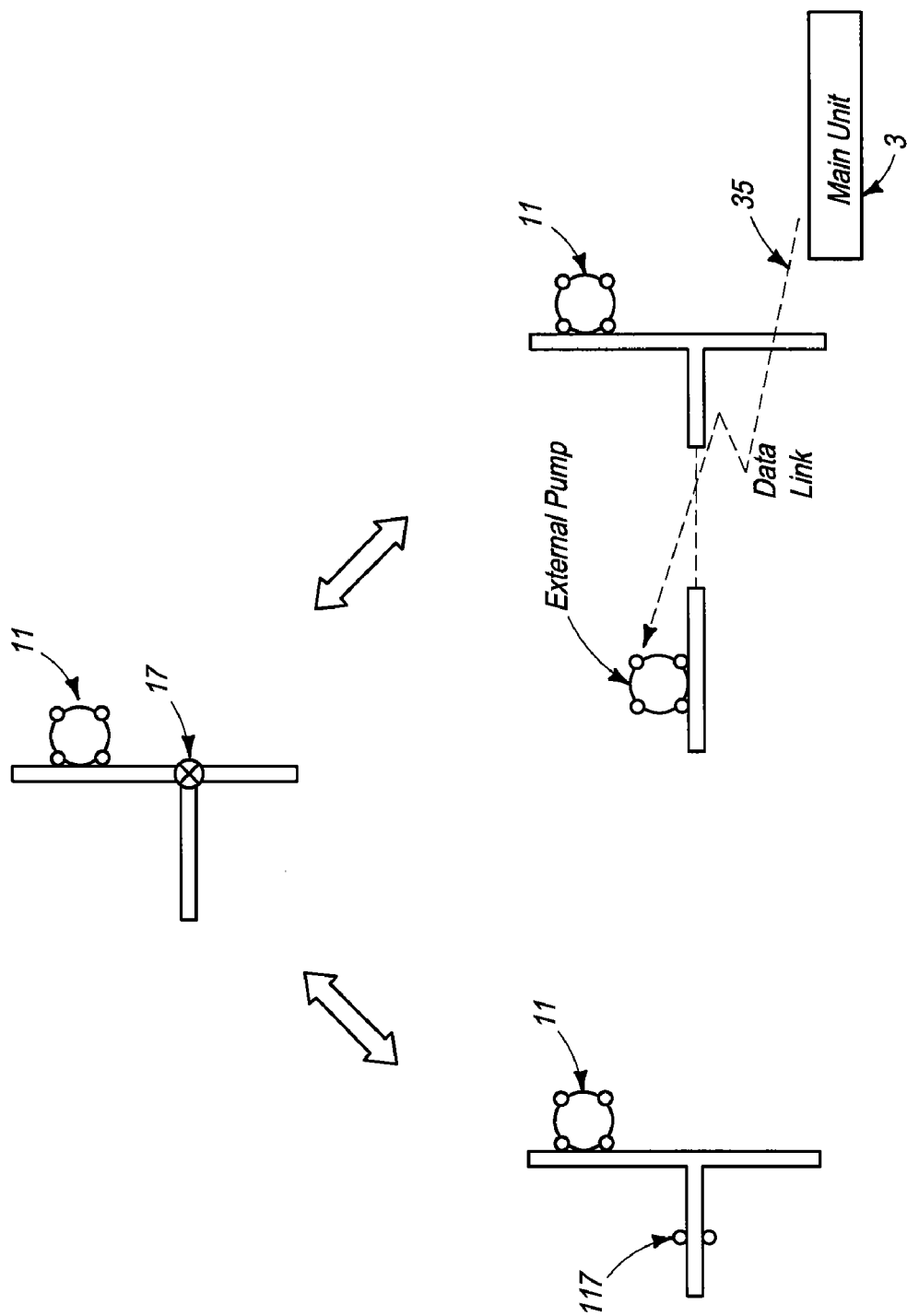

In yet another embodiment, FIGS. 10a and 10b illustrate alternative methods for controlling the flow of fluids in connection to the automated blood analysis device of the present invention, and as shown in FIGS. 1a, 1b, 1c, and 1d. Reference will again be made to FIGS. 1a, 1b, 1c, and 1d where necessary. As shown in FIG. 10a, stopcock 15 (also shown in FIGS. 1a, 1b, and 1d) can be replaced by other means of blocking line 16, which can include, but are not limited to, pump 13 or an external automatic pinching component 116. If line 16 is blocked by pump 13 (if used) or by external pinching component 116 (if used), there is no flow of fluid from the main tube to line 16. Pressure valve 115 may additionally be used in order to further ensure that no diffusion occurs between line 16 and the main tube.

As illustrated in FIG. 10b, three-way stopcock 17 (also shown in FIGS. 1a, 1b, 1c, and 1d) may be replaced by other means of blocking the external infusion. The means include, but are not limited to, an external automatic pinching component 117 on the line coming from the external infusion, or a data connection 35 between main unit 3 to the external pump controlling the external infusion. As described in detail above, if used, these alternative means ensure that external infusion is automatically stopped when a blood sample is required, and that the infusion is automatically restarted after the blood sample has been taken. An additional pressure valve (not shown) can be optionally added to the line coming from the external infusion in order to provide further disconnection between the lines.

In the following embodiments illustrated in FIGS. 11-18, multiple lumen tubing structures preferably attached to the catheter leading to the vascular access point via a standard connector are disclosed. Reference will now be made in detail to specific embodiments of the invention. While the invention will be described in conjunction with specific embodiments, it is not intended to limit the invention to one embodiment. Thus, the present invention is not intended to be limited to the embodiments described, but is to be accorded the broadest scope consistent with the disclosure set forth herein.

Now referring to FIGS. 11-18, an alternative tubing design may be used for automated fluid flow control in connection with the automated blood analysis device of the present invention. In this alternative embodiment using a multiple lumen tubing structure, the device can be placed at a greater distance from the catheter location, without a significant sacrifice of the drawn blood volume. In a preferred arrangement, the testing unit is located near the infusion pump with a tube of 1.5 m long between the testing unit and the catheter. The system can either be located on the post under the infusion fluid bag, as described in FIGS. 11a-11f, or under the infusion pump, as described in FIGS. 16a-16f. In the following embodiments, reference will only be made to the distinct differences from those embodiments described with reference to FIGS. 1-10 above. It is well understood by those of ordinary skill in the art that certain materials applied therein may also be applicable to the embodiments described below, such as, but not limited to, pump characteristics, system materials, and sensor cassette characteristics. The alternative embodiments as described with respect to FIGS. 11-18 disclose a multiple lumen tubing structure.

FIGS. 11a-11f illustrates both the system and its operational characteristics. Reference to the system components will be made with respect to FIG. 11a. FIGS. 11b-11f will be referred to when describing the operational characteristics of this embodiment.

Figure 11A:
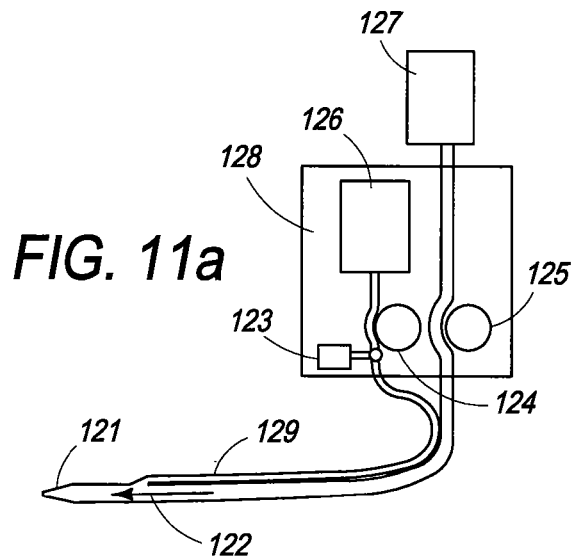
FIGS. 11a-11f illustrate both the system and operational characteristics of an alternate tubing structure used for automated fluid flow control in connection with one embodiment of the automated blood analysis device of the present invention.
Figure 11B:
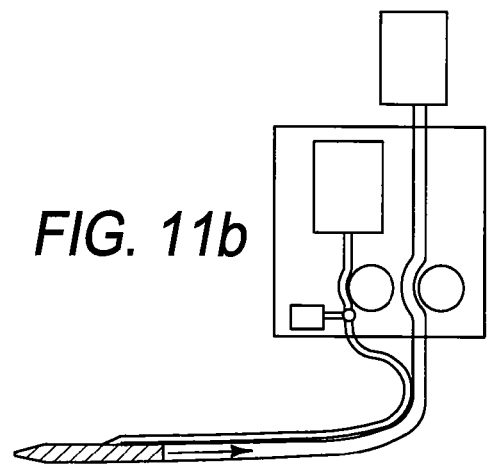

Now referring to FIG. 11a, the automated blood analysis device 128 includes all necessary pumps as described with reference to FIGS. 1a-1d above. In addition, automated blood analysis device 128 is connected to an infusion fluid bag 127 on one side and to the patient (not shown) on the other side. Automated blood analysis device 128 is similar to automated blood analysis device 1, described with reference to FIGS. 1-10 above, however, employs a multiple lumen tubing system that leads to the automated blood analysis device. It is to be understood by those of ordinary skill in the art that various components may be included in both designs of the system and that this description of the multiple lumen tube structure is not limiting. For example, automated blood analysis device 128 employs a disposable, sterile packaged sensor cassette as described with respect to FIGS. 1a-1d above. In addition, automated blood analysis device 128 also uses a main unit for control, such as that described above and referred to as main unit 3.

The catheter 121 coming out of the vascular access point, such as a vein or artery, is connected to Y (or T) junction (not visible). The connection to the catheter is accomplished via using a standard connecter, known to those of ordinary skill in the art, such as, but not limited to the connector used for connecting Venflon infusion sets. The remaining two ports of the junction are connected to two tubes, 122 and 129. First tube 122 is the standard infusion tube, known to those of ordinary skill in the art. Second tube 129 is used for drawing sample blood. In a preferred embodiment, the blood sampling tube 129 has a smaller diameter than the infusion tube, and still more preferably is of the smallest diameter possible to enable blood flow without clotting or hemolisys.

First tube 122 and second tube 129 are attached together. Thus, in this second preferred embodiment of the automated blood analysis device of the present invention, no three-way stopcock, rotating valves, or other mechanisms are needed proximate to the catheter. Further, this eliminates the need to attach the patient's hand directly to a bulky device creating a more user friendly automated blood analysis device. The dual lumen tube structure leads directly to the automated blood analysis device 128. As shown in FIG. 11a, two peristaltic pumps 124 and 125 are located in automated blood analysis device 128, one for each tube.

Figure 11C:
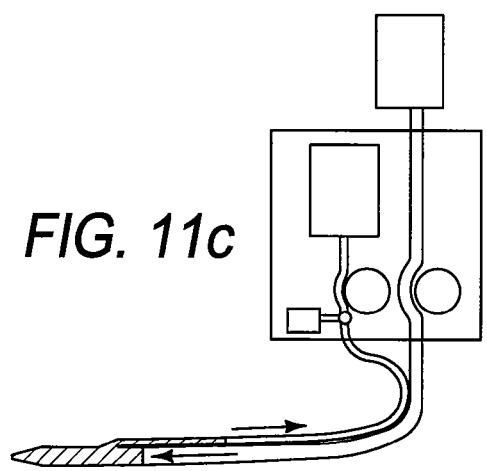

Now referring to FIGS. 11a-11f, the normal operation of infusion is described. The infusion fluid flows from infusion fluid bag 127 to the vascular access point at a rate determined by infusion pump 125. Peristaltic pump 124 is on hold at this point. As shown by the arrow in FIG. 11b, when it is determined that a blood sample is needed, pump 125 reverses its direction and draws a small bolus of blood, ensuring that an undiluted blood sample passes the Y (or T) junction. As shown in FIG. 11c, pump 124 begins to draw the blood bolus through the smaller of the two tubes 129. As shown by the arrows in FIG. 11c, pump 125 pushes back the infusion fluid at the same rate at which pump 124 draws blood. Thus, the blood in first tube 122 is not moving.

Figure 11D:
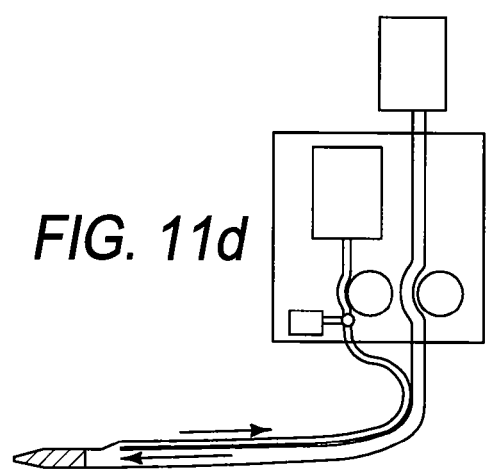

After a large enough bolus of blood enters into tube 129, as shown in FIG. 11d, pump 124 still works at the same rate, while pump 125 increases its flow rate substantially enough such that the blood held in the catheter 121 is infused back to the body and the blood bolus in thin tube 129 moves up toward the sensing device 123.

Figure 11E:
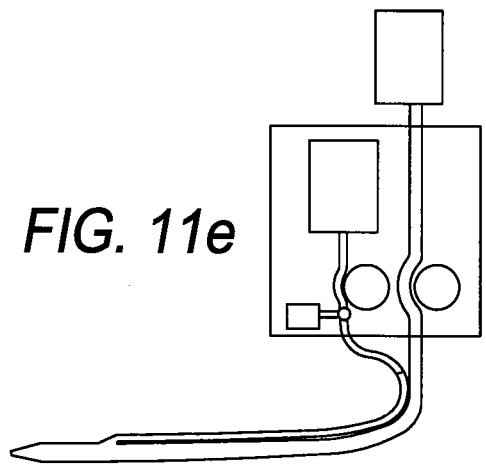
Figure 11F:
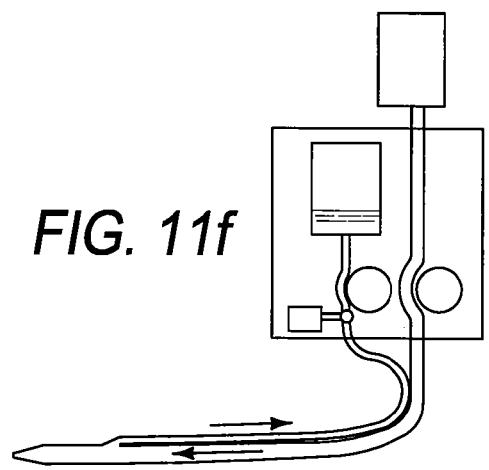

The testing step is illustrated in FIG. 11e. Here, pump 124 stops operation and a valve or other mechanism on thin tube 129 (shown as a small circle) is opened to allow for a small volume of blood to travel towards the sensing device 123. Sensing device 123 has already been described in great detail with reference to sensor cassette 5 above and will not be discussed in further detail herein. It is to be understood by one of ordinary skill in the art that the sensor devices as described above are equally applicable to the embodiment described herein. When the blood measurement is complete, pump 124 resumes operation and the remaining blood bolus in thin tube 129 is flushed into waste bag 126, as shown in FIG. 11f.

Optionally, the measurement stage as shown in FIG. 11d is skipped and the blood bolus is drawn through thin tube 129 to sensing device 123. Thus, pump 125 is not operated to push the infusion fluid. If this option is exercised, a narrower tube is used for drawing the blood, such as, but not limited to a 0.5 mm diameter tube. In using such a thin tube, filling 2 m of the tube only requires 0.4 cc of blood. FIG. 12 illustrates a table of blood bolus volumes in cubic centimeters according to the tube diameter in mm and its length in cm.

The blood measurement method described in FIGS. 11a-11f can also optionally be implemented by an external unit add-on box that contains the sensing device 128 and controls a commercial dual channel infusion pump that fulfills the functionality of both pumps 124 and 125.

As shown in FIGS. 13a-13f, the automated blood analysis device of the present invention may also be implemented using a single channel infusion pump 125 and an additional controlled valve 133. In this configuration, the two tubes coming from the Y (or T) junction have the same diameter. Thus, when the valve 133 is rotated to connect only those two tubes, as shown in FIG. 13c, and communication with the infusion fluid bag is shut off completely, the blood bolus is circulated in an effectively closed loop tube. The circulatory pattern is shown in FIGS. 13c and 13d. As shown in FIG. 13e, the blood is tested by the sensing device 123. FIG. 13f illustrates the flushing of the remaining blood bolus into waste bag 126.

Figure 14:
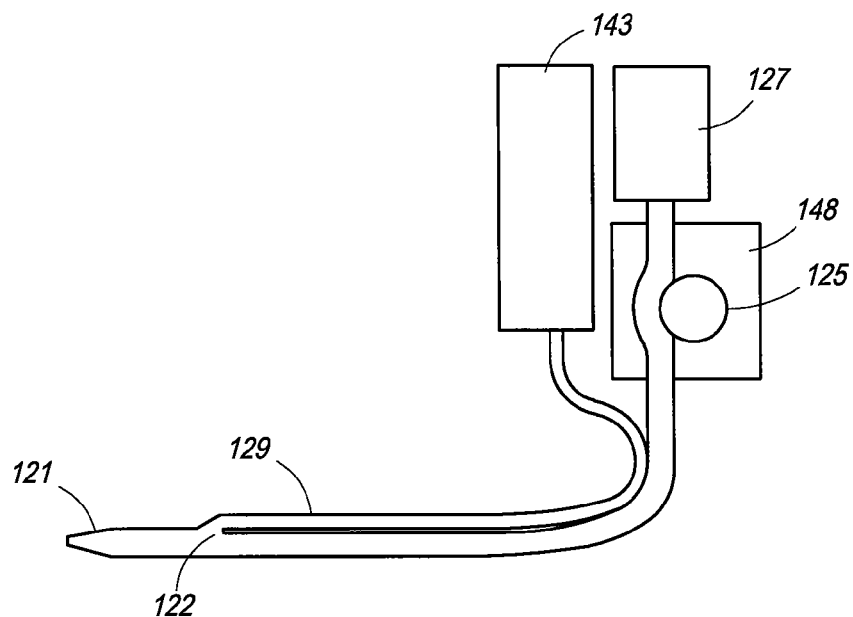
FIG. 14 illustrates an automated blood analysis device, such as that shown in FIGS. 11a-11f implemented with a single channel external infusion pump.

Now referring to FIG. 14, a device similar to that described above with reference to FIGS. 11a-11f is shown, however, the device is implemented with a single channel external infusion pump 148. Add-on device 143 comprises the second pump (not shown), sensing device (not shown), and waste bag (not shown). operationally, the device functions is the same manner as the configuration shown in FIGS. 11a-11f. The add-on device 143 controls the infusion pump 148 by means of an electrical connection.

Figure 15:
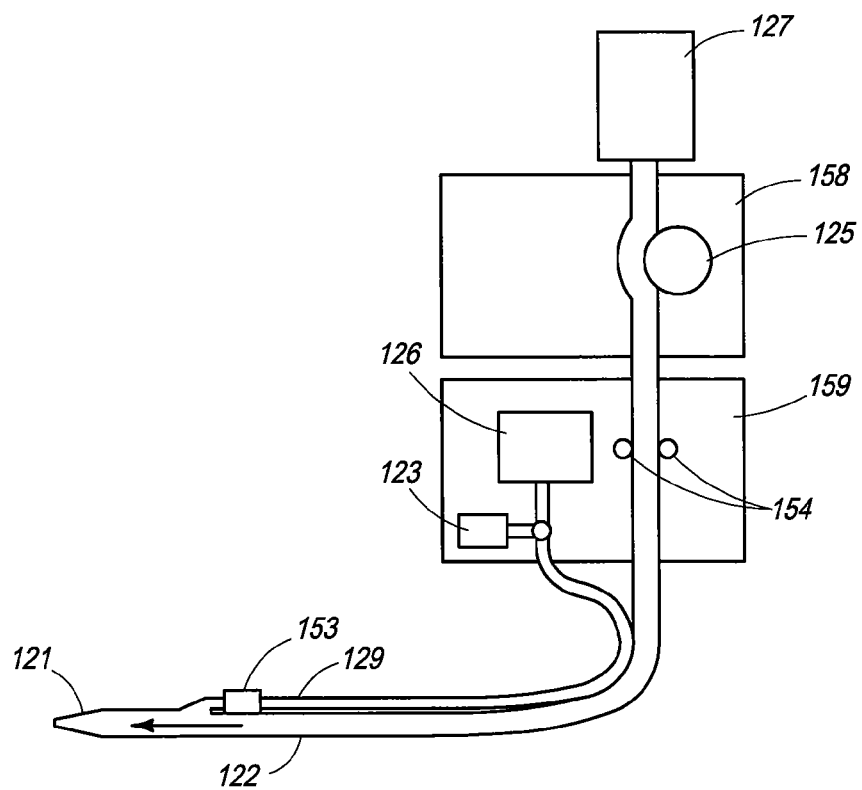
FIG. 15 illustrates a device similar to that described with reference to FIGS. 11a-11f, wherein the infusion fluid is stopped by pinching the tubing with two members.

In yet another embodiment, FIG. 15 illustrates a device similar to that described with reference to FIGS. 11a-11f, however, the need for an electrical connection with infusion pump 158 is eliminated. In this embodiment, the infusion fluid is stopped by pinching the tubing with two rods 154. The diluted blood in the vein flows and the waste bag 126 begins to draw blood until an undiluted blood sample approaches near the valve of sensing device 153. When the measurement is complete, the blood is flushed into waste bag 126.

FIGS. 16a-16f depicts yet another embodiment of the automated blood analysis device of the present invention. In this implementation, the need for controlling the infusion pump is eliminated. In addition, however, it does not initiate the blockage alarm of the infusion pump and it reduces the required amount of blood drawn by returning the diluted blood portions back into the vascular access point, as with the embodiment described with respect to FIGS. 11a-11f.

Figure 16A:
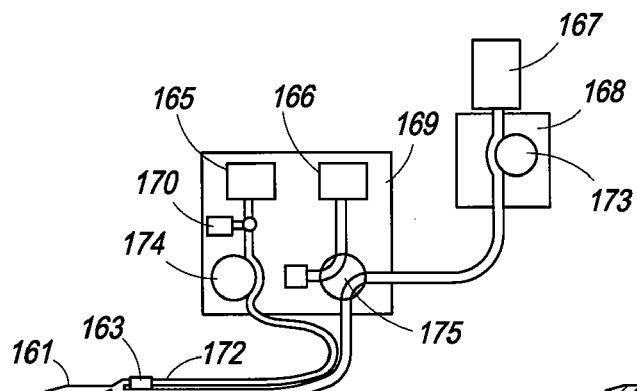
FIGS. 16a-16f depict yet another alternate embodiment of the automated blood analysis device of the present invention, without infusion pump control.

As shown in FIG. 16a, the catheter 161 coming out of the vascular access point, such as a vein or artery is connected to a Y (or T) junction (not visible). The connection to the catheter is accomplished via using a standard connecter, known to those of ordinary skill in the art, such as, but not limited to the connector used for connecting Venflon infusion sets. The two other ports of the junction are connected to two tubes, 162 and 172. First tube 162 is the standard tube used for infusion as are well-known to those of ordinary skill in the art. Second tube 172 is used for drawing sample blood, and is connected to the junction with a valve, which can optionally be unidirectional. In a preferred embodiment, the blood sampling tube 172 has a smaller diameter than the infusion tube, and still more preferably is of the smallest diameter possible to enable blood flow without clotting or hemolisys. First tube 162 and second tube 172 are attached together. The dual lumen tube leads directly into automated blood analysis device 169, as shown in FIG. 16a. The infusion tube continues from the automated blood analysis device 169 to the standard infusion pump 168 and infusion fluid bag 167.

Figure 16B:
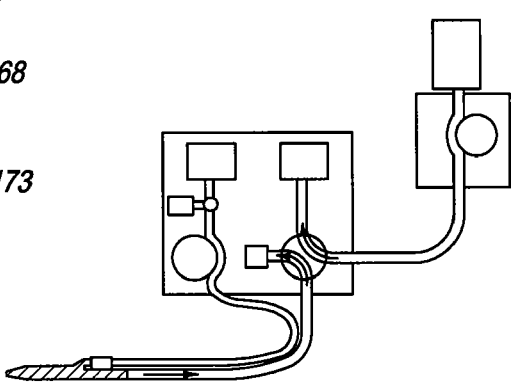

Now referring to FIGS. 16a-16f, the normal operation of infusion is described. The infusion fluid flows from infusion fluid bag 167 to the vascular access point, at a rate determined by pump 173. At this point, pump 174 is non-operational. When it is determined that a blood sample is needed, the four-way stopcock 175 rotates 90° as shown in FIG. 16b. Thus, the infusion pump 173 is now connected to empty infusion bag 166 and the infusion tube 162 is connected to syringe pump 171. Infusion pump 173 continues operation and infuses infusion fluid into empty infusion bag 166. Syringe pump 171 draws a small bolus of blood out of the vascular access point, as required so that an undiluted blood sample approaches the Y (or T) junction, as shown in FIG. 16b. The flow rate of the blood draw is so enough to ensure that the catheter does not collapse.

Figure 16C:
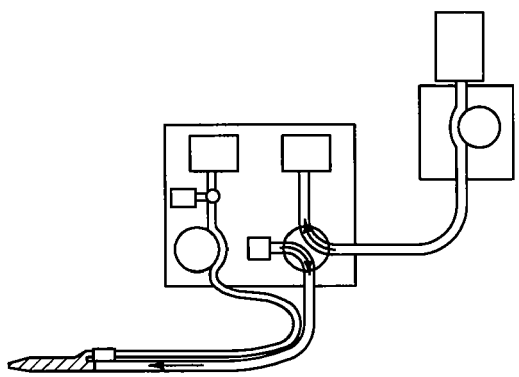

As shown in FIG. 16c, pump 174 starts to draw the blood bolus into the smaller tube 172. Syringe pump 171 pushes back infusion fluid at the same rate of flow as pump 174 draws blood. Thus, the blood collected in catheter 161 is not moving.

Figure 16D:
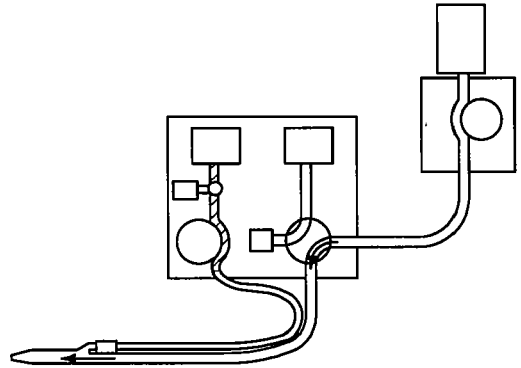

After a large enough bolus of blood enters into tube 172, pump 174 still works at the same rate, while syringe pump 171 increases its flow rate substantially enough such that the blood held in the catheter 161 is infused back to the body and the blood bolus in thin tube 172 moves up toward the sensing device 170. Subsequently, the four-way stopcock 175 rotates back by 90° while the infusion fluid from the infusion pump flows back to the vascular access point, as shown in FIG. 16d. Again, the blood bolus length in tube 172 is large enough such that its center is not diluted with infusion fluid. While valve 175 is in this position, the infusion fluid accumulated at infusion fluid bag 166 can be transferred into syringe pump 171 and from there back to the vascular access point on the next blood sampling period. This concept is important, as the infusion fluid may contain medications, and thus, its infused amount should be kept even when interrupted by blood sampling. In addition, infusion fluid bag 166 is kept empty and thus reduces its volume requirements.

Figure 16E:
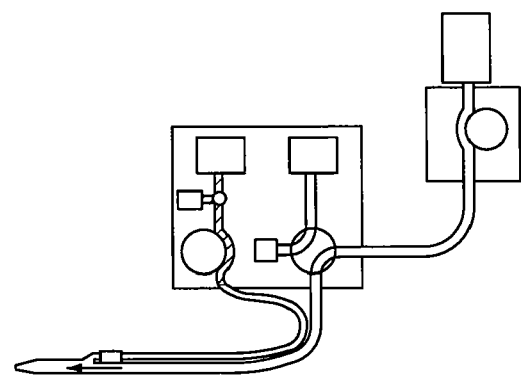
Figure 16F:
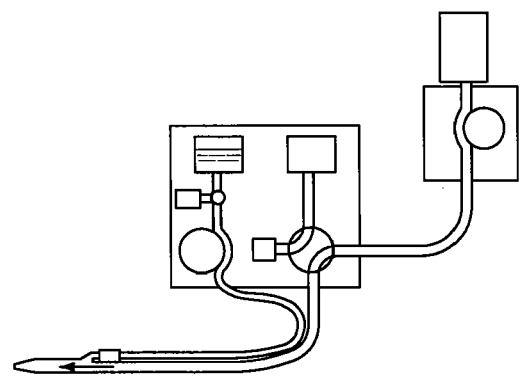

The testing step is illustrated in FIG. 16e. Here, pump 174 stops operation and a valve or other mechanism on thin tube 172 (shown as a small circle) is opened to allow for a small volume of blood to travel towards the sensing device 170. Sensing device 170 has already been described in great detail with reference to sensor cassette 5 above and will not be discussed in further detail herein. It is to be understood by one of ordinary skill in the art that the sensor devices as described above are equally applicable to the embodiment described herein. When the blood measurement is complete, pump 174 resumes operation and the remaining blood bolus in thin tube 172 is flushed into waste bag 165, as shown in FIG. 16f.

Optionally, the measurement stage as shown in FIG. 16d is skipped and the blood bolus is drawn through thin tube 172 to sensing device 170. Thus, pump 173 is not operated to push the infusion fluid. If this option is exercised, a narrower tube is used for drawing the blood, such as, but not limited to a 0.5 mm diameter tube. In using such a thin tube, filling 2 m of the tube only requires 0.4 cc of blood.

Figure 17:
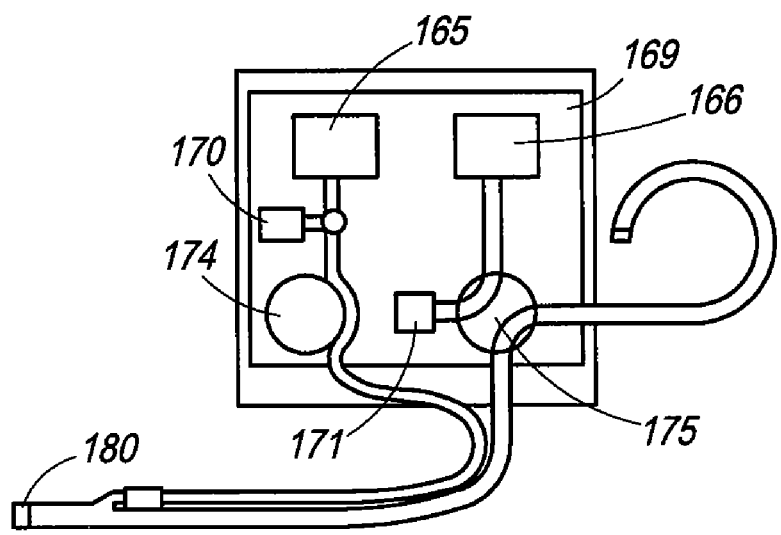
FIG. 17 illustrates the disposable portion of the automated blood analysis device in one arrangement.

FIG. 17 illustrates the disposable portion of the automated blood analysis device in another embodiment. Vascular access point 180 is connected to the catheter via a connector. The tube 181 passes through the infusion pump 175, which is connected to the infusion fluid bag. The set is sterile prior to connection to the vascular access point. The tubes are pre-connected to the disposable measurement portions of the device. After the system is connected to the infusion bag and infusion pump, the system fills the tube with infusion fluid automatically.

Figure 18:
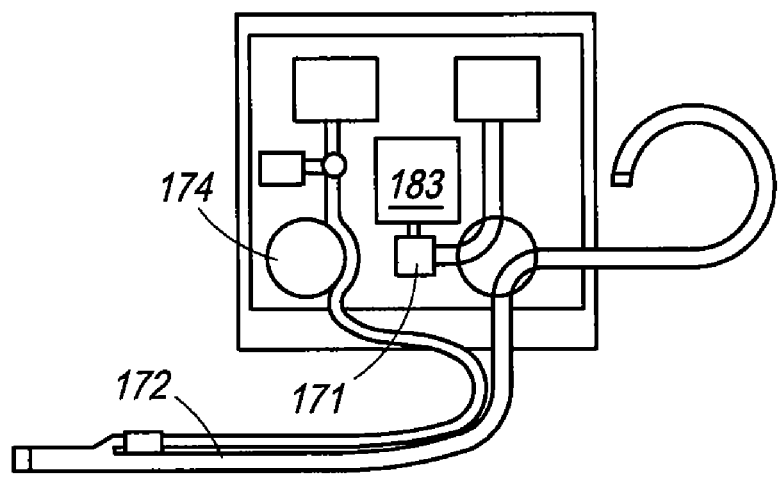
FIG. 18 depicts another optional embodiment of the automated blood analysis device, wherein a saline bag is added to the system for self-flushing.

In another embodiment of the automated blood analysis device, as shown in FIG. 18, a saline bag 183 is added to the system for self flushing without reliance on the external infusion fluid that may contain medication. Saline bag 183 is connected to the infusion tube via pump 171 in the flushing step and pump 174 draws it into the thin tube 172 for flushing the thin tube. The blood and saline mixture is flushed into waste bag 166.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

We claim:

1. A device for periodically monitoring at least one parameter of blood from a patient, comprising:
    an access device configured to access blood in a patient;
    a fluid channel system connectable to the access device;
    a pump configured to transport blood through the fluid channel system;
    a dispenser connectable to the fluid channel system and configured to dispense a blood sample; and
    a plurality of test substrates in a cassette or cartridge;
    at least one movable sample reservoir configured to separate from the dispenser and to transport the blood sample towards a test substrate in the cassette or cartridge;
    a sensor configured to analyze the test substrate and produce a sensor signal indicative of at least one parameter; and
    a signal processor configured to receive the sensor signal.

2. The device of claim 1, wherein the dispenser is contained in the cassette or cartridge.

3. The device of claim 2, wherein the plurality of test substrates are single use test substrates.

4. The device of claim 3, wherein the at least one parameter is a blood glucose level, ketone level, hemoglobin level, lactate level, electrolyte level, blood gas level, cholesterol level.

5. The device of claim 3, wherein the sensor is pre-calibrated.

6. The device of claim 1, further comprising at least two sensors of different modalities, and wherein at least two sensor signals are configured to produce at least two sensor signals and the signal processor is configured to generate a measurement signal from the at least two sensor signals.

7. The device of claim 1, wherein said device is configured to automatically withdraw blood and wherein the fluid channel system is configured to connect to at least one external line capable of being used for external infusion.

8. The device of claim 1, wherein a portion of the fluid channel system comprises a multiple-lumen tube.

9. The device of claim 1, wherein the signal processor is configured to generate a measurement signal and communicate said measurement signal to a therapy device configured to deliver therapy based on said measurement signal.

10. The device of claim 1, further comprising a test substrate advancing mechanism.

11. A method for periodically monitoring at least one parameter of blood from a patient, comprising:
    withdrawing blood from a patient;
    transporting the blood through a fluid channel system to a dispenser;
    dispensing a sample of the blood through a dispenser to a movable sample reservoir;
    separating the movable sample reservoir and the sample from the dispenser;
    subsequently transporting the sample via the movable sample reservoir to a first test substrate located in a cassette or cartridge;
    analyzing the test substrate with a sensor and producing a sensor signal indicative of at least one parameter; and
    receiving and processing the sensor signal.

12. The method of claim 11, wherein the dispenser is contained in the cassette or cartridge.

13. The method of claim 12, wherein the first test substrate is a single use test substrate.

14. The method of claim 13, wherein at least one parameter is a blood glucose level, ketone level, hemoglobin level, hematocrit level, lactate level, electrolyte level, blood gas level, cholesterol level, or bilirubin level.

15. The method of claim 13, wherein the sensor is pre-calibrated.

16. The method of claim 11 further comprising at least two sensors of different modalities, and wherein the at least two sensor signals are configured to produce at least two sensor signals and the signal processor is configured to generate a measurement signal from the at least two sensor signals.

17. The method of claim 11, wherein said device is configured to automatically withdraw blood and wherein the fluid channel system is configured to connect to at least one external line capable of being used for external infusion.

18. The method of claim 11, wherein a portion of the fluid channel system comprises a multiple-lumen tube.

19. The method of claim 11, wherein the signal processor is configured to generate a measurement signal and communicate said measurement signal to a therapy device configured to deliver therapy based on said measurement signal.

20. The method of claim 11, further comprising advancing a second test substrate to the dispensing position.

21. The method of claim 11, wherein the withdrawing of blood from the patient is done in a predetermined time schedule.

* * * * *